(12) United States Patent
Morrell

(10) Patent No.: US 7,353,065 B2
(45) Date of Patent: Apr. 1, 2008

(54) RESPONSIVE THERAPY FOR PSYCHIATRIC DISORDERS

(75) Inventor: Martha Morrell, Portola Valley, CA (US)

(73) Assignee: NeuroPace, Inc., Mountain View, CA (US)

( * ) Notice: Subject to any disclaimer, the term of this patent is extended or adjusted under 35 U.S.C. 154(b) by 100 days.

(21) Appl. No.: 10/941,759

(22) Filed: Sep. 14, 2004

(65) Prior Publication Data
US 2006/0058856 A1    Mar. 16, 2006

(51) Int. Cl.
A61N 1/05    (2006.01)

(52) U.S. Cl. ...................................... 607/45

(58) Field of Classification Search ................. 607/45
See application file for complete search history.

(56) References Cited

U.S. PATENT DOCUMENTS

| | | | |
|---|---|---|---|
| 6,016,449 A * | 1/2000 | Fischell et al. | 607/45 |
| 6,109,269 A | 8/2000 | Rise et al. | |
| 6,128,537 A | 10/2000 | Rise | |
| 6,176,242 B1 | 1/2001 | Rise | |
| 6,263,237 B1 | 7/2001 | Rise | |
| 6,354,299 B1 * | 3/2002 | Fischell et al. | 128/899 |
| 6,473,639 B1 * | 10/2002 | Fischell et al. | 600/544 |
| 6,591,138 B1 * | 7/2003 | Fischell et al. | 607/45 |
| 6,597,954 B1 | 7/2003 | Pless et al. | |
| 6,609,030 B1 | 8/2003 | Rezai et al. | |
| 6,708,064 B2 | 3/2004 | Rezai | |
| 6,810,285 B2 | 10/2004 | Pless et al. | |
| 2002/0013612 A1 * | 1/2002 | Whitehurst | 607/45 |
| 2002/0151939 A1 | 10/2002 | Rezai | |
| 2003/0036781 A1 | 2/2003 | Nuttin et al. | |
| 2003/0149457 A1 * | 8/2003 | Tcheng et al. | 607/48 |
| 2004/0138518 A1 | 7/2004 | Rise et al. | |
| 2004/0172091 A1 | 9/2004 | Rezai | |
| 2005/0027284 A1 | 2/2005 | Lozano et al. | |
| 2005/0033379 A1 | 2/2005 | Lozano et al. | |

OTHER PUBLICATIONS

Weiland and Anderson, "Chronic Neural Stimulation with Thin-Film, Iridium Oxide Electrodes," IEEE Transactions on Biomedical Engineering, 47: 911-918 (2000).

* cited by examiner

*Primary Examiner*—Kennedy J. Schaetzle
*Assistant Examiner*—Yun Haeng Lee

(57) ABSTRACT

An implantable neurostimulator system for treating psychiatric disorders includes scheduled and responsive therapy capabilities including responsive stimulation applied to the cingulate gyrus of the brain. Methods for treating depression, bipolar disorder, anxiety and obsessive-compulsive disorders, post-traumatic stress disorder, addiction, schizophrenia, and autism and other developmental disorders employ an inventive system to advantageously reduce symptoms and address underlying causes of the disorders.

8 Claims, 18 Drawing Sheets

RESPONSIVE THERAPY FOR PSYCHIATRIC DISORDERS

FIELD OF THE INVENTION

The invention relates to systems and methods for treating brain disorders, and more particularly to treating neuropsychiatric disorders and related diseases with automatically delivered therapies.

BACKGROUND OF THE INVENTION

Severe affective and behavioral psychiatric disorders affect 5 to 10 million adults in the United States and are the leading cause of disability in North America and Europe. Men and women of all ages and races are at risk for mental illness and for the associated morbidity and societal cost. Although psychopharmacological therapy provides at least partial relief for between 70 to 90% of persons suffering from major depression, bipolar disorder (BPD), obsessive-compulsive disorder (OCD) and panic and other severe anxiety disorders; others are not helped or experience unacceptable medication related side effects. Those experiencing schizophrenia, episodic behavioral disorders, post-traumatic stress disorder (PTSD), addictions, and the behavioral and social disorders associated with autism and pervasive developmental disorders are less often helped by pharmacotherapy or psychotherapy. The economic cost of untreated mental illness is more than 100 billion dollars each year in the United States.

Accordingly, new treatments are clearly needed for those whose symptoms persist and for those not tolerating therapy, as well as to relieve the societal burden created by untreated and under treated mental illness.

Major depression is a serious and persistent medical illness affecting 9.9 million American adults, or approximately 5 percent of the adult population in a given year. Among all medical illnesses, major depression is the leading cause of disability in the U.S. and many other developed countries. About three-fourths of those who experience a first episode of depression will have at least one other episode in their lives and some individuals have several episodes in the course of a year. If untreated, episodes commonly last anywhere from six months to a year. Left untreated, depression can lead to suicide.

Treatment typically includes medications, psychotherapy, and electroconvulsive therapy (ECT) used singly or in combination. Although mild to moderate depression can often be treated successfully with medications or psychotherapy used alone, severe depression usually requires a combination of psychotherapy and medication. ECT is highly effective for treatment resistant or treatment intolerant severe depression and to relieve symptoms such as psychosis or thoughts of suicide. However, ECT often requires repeated therapies and can cause persistent and troubling memory disturbances.

Bipolar disorder is another other common major psychiatric disorders that may be treatment resistant. Bipolar disorder is a chronic disorder that affects 2.3 million adult Americans. Bipolar disorder is characterized by episodes of mania and depression that can last from days to months. Persons with bipolar disorder usually require lifelong treatment, and recovery between episodes is often poor. Generally, those who suffer from bipolar disorder have symptoms of both mania and depression (sometimes at the same time). Medications are available to treat depression or mania and provide mood stabilization. However, most persons with bipolar disorder require multiple medications to achieve symptom relief. Thus, persons with bipolar disease are at risk for medication related side effects that prompt some to discontinue therapy. Others who are compliant with therapy do not achieve complete symptom relief.

Obsessive-Compulsive Disorder (OCD) affects 2 to 3% of the population as confirmed in the U.S. and international epidemiological studies, and is two to three times more common than schizophrenia and bipolar disorder. Obsessions and compulsive behaviors can cause suffering and severe restrictions on life activities. Response to treatment varies from person to person. Most people treated with effective medications find their symptoms reduced by about 40 percent to 50 percent. Although such symptom relief is welcome, freedom from symptoms is rarely achieved and only a small number of people are fortunate to go into total remission. Only one fifth of patients achieve full remission within one decade of the onset of the illness and two-thirds continue to experience symptoms despite treatment with selective serotonin reuptake inhibitor drugs (SSRIs) and the use of behavior therapy.

Some persons with chronic, treatment resistant mental illness have turned to surgical therapies. Frontal lobotomy was championed in the late 1930s to the 1970s. Although effective in some cases, the surgery was crude, not standardized and involved destruction of a large region of the frontal lobe. The procedure was largely abandoned because of unacceptable surgical complications and because of ethical violations in its application. A few centers continued to offer surgical therapy to the most devastated patients. The National Commission for the Protection of Human Subjects of Biomedical and Behavioral Research (1977) indicated that more than half of 400 surgeries performed annually between 1971 and 1973 for psychiatric indications were efficacious, and there is reason to believe efficacy has improved since then.

Recently, neurosurgeons have developed more precise surgical procedures to treat psychiatric disorders, including depression and, more commonly, obsessive-compulsive disorder. The majority of these procedures involve targeted ablative procedures. In these refractory patients, stereotactic surgical interventions performed include subcaudate tractotomy, limbic leucotomy, capsulotomy, and cingulotomy. Cingulotomy is the most commonly performed procedure. Twentyfive to 30% of patients treated with cingulotomy experience improvement at more than 2 years follow-up. However, these procedures are associated with risks including changes in personality and development of epilepsy. Other adverse effects include frontal lobe deficit in as many as 30% with fatigue, emotional blunting, emotional incontinence, indifference, low initiative, disinhibition and impaired judgment. These procedures carry the risk that the lesion will be malpositioned, which may require repeated surgery to extend the size of the lesion. Thus, concerns about safety and the irreversibility of surgical procedures remain.

Due to the limited response to lesion-based surgery and concerns about adverse effects, some investigators have turned to electrical stimulation therapy. Building on the experience from essential tremor and Parkinson's Disease, investigators have utilized commercially available deep brain stimulators implanted in the anterior internal capsule bilaterally and have reported symptomatic improvement in OCD. However, because of the stimulation requirements for clinical response (4 to 10.5V, impedance 700 ohms, pulse width 210 microseconds, 100 Hz frequency) the stimulator battery requires replacement every 5 to 12 months, limiting patient acceptance for this therapy.

The neuroanatomical base for many psychiatric disorders is better understood because of advances in functional neuroimaging, such as Positron Emission Tomography (PET), Magnetic Resonance Imaging (MRI), Functional MRI (fMRI), and Magnetoencephalography (MEG). In addition, clinical observations after destructive brain lesions identify regions subserving specific aspects of behavior and affect. The cingulate cortex is a large structure around the rostrum of the corpus callosum that has extensive projections with the amygdala, periaqueductal grey, ventral striatum, orbitofrontal and anterior insular cortices. This structure and its interconnections are intimately involved in mood and behavior. Dysfunction of the cingulate and disruption of its connections has been implicated in a number of psychiatric disorders. As noted above, cingulotomy is the most common psychosurgery procedure for major depression and obsessive-compulsive disorder. This procedure is effective for many but carries considerable risk for post-surgical changes in personality and motivation, and for post-operative epilepsy.

The size and complexity of the cingulate cortex poses a challenge in targeting the region responsible for specific psychiatric and behavioral disorders. The cingulate is divided functionally into regions concerned with affect and cognition. Affect is mediated in cingulate regions 25, 33 and rostral area 24 that are extensively interconnected to the amygdala and periaqueductal grey, as well as autonomic brainstem nuclei. The cognitive division resides in caudal areas 24' and 32', and in cingulate motor areas in the cingulate sulcus and nociceptive cortex. Individuals with disturbances to the cingulate cortex, such as those with cingulate onset epilepsy, often display sociopathic behavior. Elevated anterior cingulate activity may contribute to tics, obsessive-compulsive behaviors and aberrant social behavior. Reduced cingulate activity can contribute to schizophrenia, behavioral disorders such as akinetic mutism, diminished self-awareness and depression, motor neglect and impaired initiation of movement, reduced pain response and abnormal social behavior.

There is a need for a responsive implantable system capable of ameliorating the symptoms of, and in some cases the underlying causes of, various psychiatric disorders.

SUMMARY OF THE INVENTION

Modulation of the function of the cingulate cortex can alleviate symptoms associated with psychiatric disorders believed to arise because of functional or structural abnormalities of this structure. Research indicates that a number of psychiatric disease are mediated through the cingulate cortex, including major depression, obsessive compulsive disorder, panic and anxiety disorders, explosive behavior disorder, post-traumatic stress disorder, substance addiction and schizophrenia. Dysfunction of the cingulate cortex is also implicated in the social disability associated with autism and pervasive developmental disorders.

In systems and methods according to the present invention, therapy for the psychiatric diseases set forth above is provided by means of a device that is able to provide responsive and programmed electrical stimulation to the cingulate cortex and other relevant portions of the brain and peripheral nervous system.

In an embodiment of the invention, a device is implanted in the cranium and attached to leads with electrodes at the distal end of each lead. The electrodes are placed within or against the entire length of cingulate cortex, whether in the form of a depth electrode or a subdural electrode. A single electrode or multiple electrodes may be implanted.

The device has a sensing function that responds to changes in a biological marker. Such biological markers could be changes in electrical activity, changes in concentration of inhibitory or excitatory neurochemicals, changes in proteins or other gene products, or changes in temperature or markers of metabolic rate. Sensing electrodes are placed over the cingulate cortex or at a distance.

Responsive therapy is provided at some location within the cingulate cortex. Such therapy may include a depolarizing electrical stimulation, drug delivery or changes in temperature. In addition, therapy delivery can be programmed by the physician in response to the patient's symptoms. The device also includes the capability for therapy to be triggered by the patient.

Such a device system could provide benefit for those individuals with treatment resistant psychiatric illness and for those who experience drug related side effects that limit quality of life. In addition, a device therapy as described above can be anticipated to have a more favorable safety profile than cortical resection or cortical lesion, and will be modifiable across individuals and over time and is reversible if the desired effects are not achieved.

The precise region of the cingulate cortex over which therapy is optimally applied may differ from individual to individual and by the psychiatric or behavioral disorder. The proposed electrode array affords wide coverage of the cingulate. Also, the electrodes over which therapy is applied can be adjusted according to the patient's short and long-term response.

The device provides continuous monitoring of electrocorticographic signals. This capability can identify disturbances in brain electrical activity over the cingulate gyrus, which is a region that can not be adequately monitored by scalp EEG due to it's distance from the recording electrodes and the significant filtering effect of skull and scalp. This is an especially important capability of the system because psychiatric disorders are likely to be accompanied by dynamic electrographic disturbances. This device will also enable continuous monitoring of other biological markers that may reveal signals of disease and disease symptoms. Identifying these biological markers will contribute to knowledge regarding the underlying pathophysiology of these diseases and will provide information that may open new avenues for targeted therapy.

Direct cortical stimulation of the cingulate cortex using a device according to the invention provides advantages over resective and lesion-based surgery and over deep-brain stimulation. Targeted cortical stimulation (as opposed to the high amount of energy required to achieve symptom relief from stimulation of anterior capsule electrodes) promises longer battery life. As described above, an exemplary device utilizes two leads of four electrodes each. Using either depth or subdural leads (or a combination of the two), electrodes can be applied over much of the cingulate cortex bilaterally. Optimal stimulation electrodes can be configured over time as a patient's symptoms are observed. Stimulation may be quite focal, using adjacent electrodes as anode and cathode, or can be applied to both left and right cingulate cortices simultaneously by utilizing all eight electrodes referred to the can of the device.

Another advantage of the implantable neurostimulator system is the capacity to apply modifiable stimulation settings. In an embodiment of the invention, pulse widths can be set between 40 and 1000 microseconds, pulse frequency may range between 1 and 333 Hz, and current can be adjusted between 0.5 and 12 milliamps. This ensures that patients receive the optimal pulse settings without adverse effects. It is reasonable to assume that individual patients will differ in terms of the optimal stimulus settings. A practitioner of ordinary skill would be able to make adjustments to these parameters based on clinical observations.

BRIEF DESCRIPTION OF THE DRAWINGS

These and other objects, features, and advantages of the invention will become apparent from the detailed description below and the accompanying drawings, in which.

DETAILED DESCRIPTION OF THE INVENTION

The invention is described below, with reference to detailed illustrative embodiments. It will be apparent that a system according to the invention may be embodied in a wide variety of forms. Consequently, the specific structural and functional details disclosed herein are representative and do not limit the scope of the invention.

Figure 1:
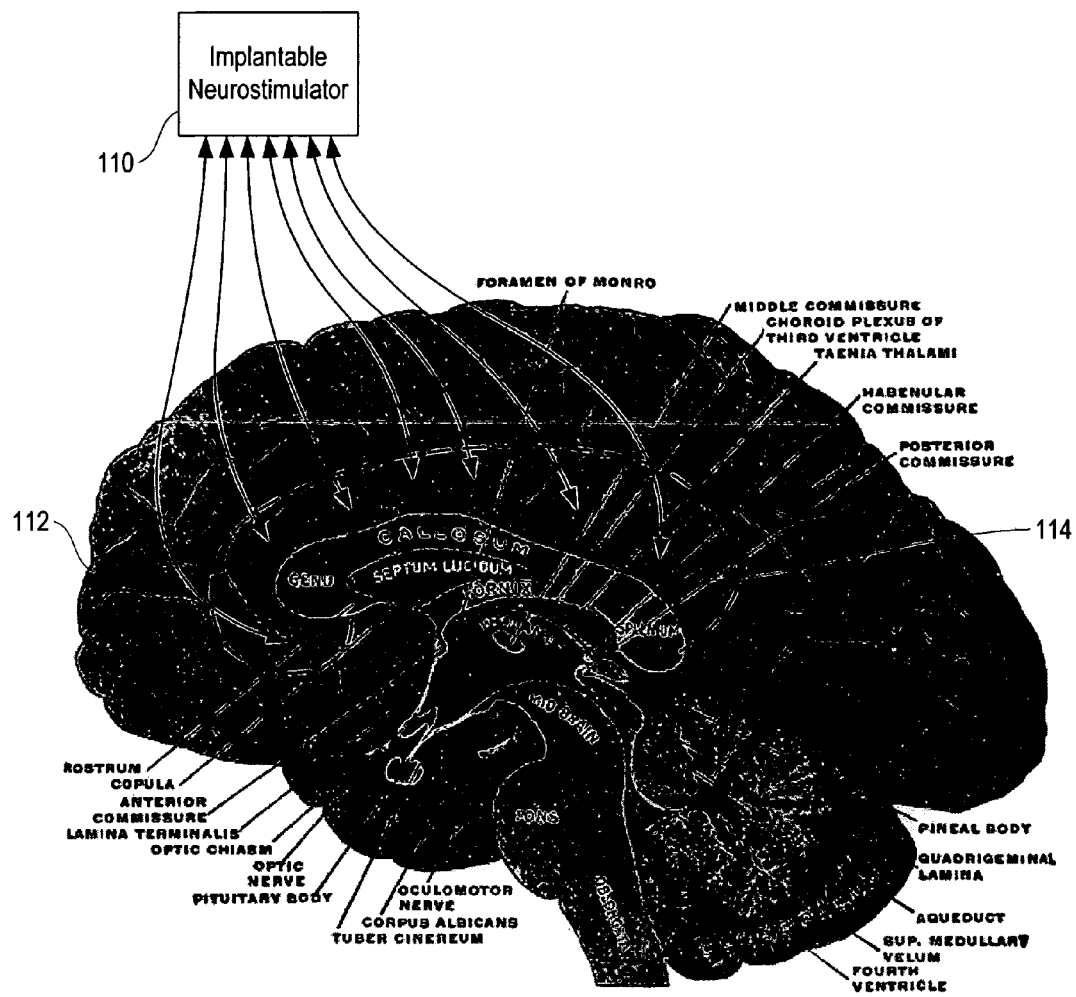
FIG. 1 is a drawing of a neurostimulator device according to the invention in communication with an exemplary brain hemisphere including the cingulate gyrus.

FIG. 1 illustrates, schematically, an implantable neurostimulator device 110 in communication with various locations within a patient's brain 112, particularly the cingulate gyrus 114. In a system according to the invention the neurostimulator device receives signals from the patient's brain 112 (or other physiological indicators) and responsively treats symptoms or conditions of psychological illness.

Figure 2:
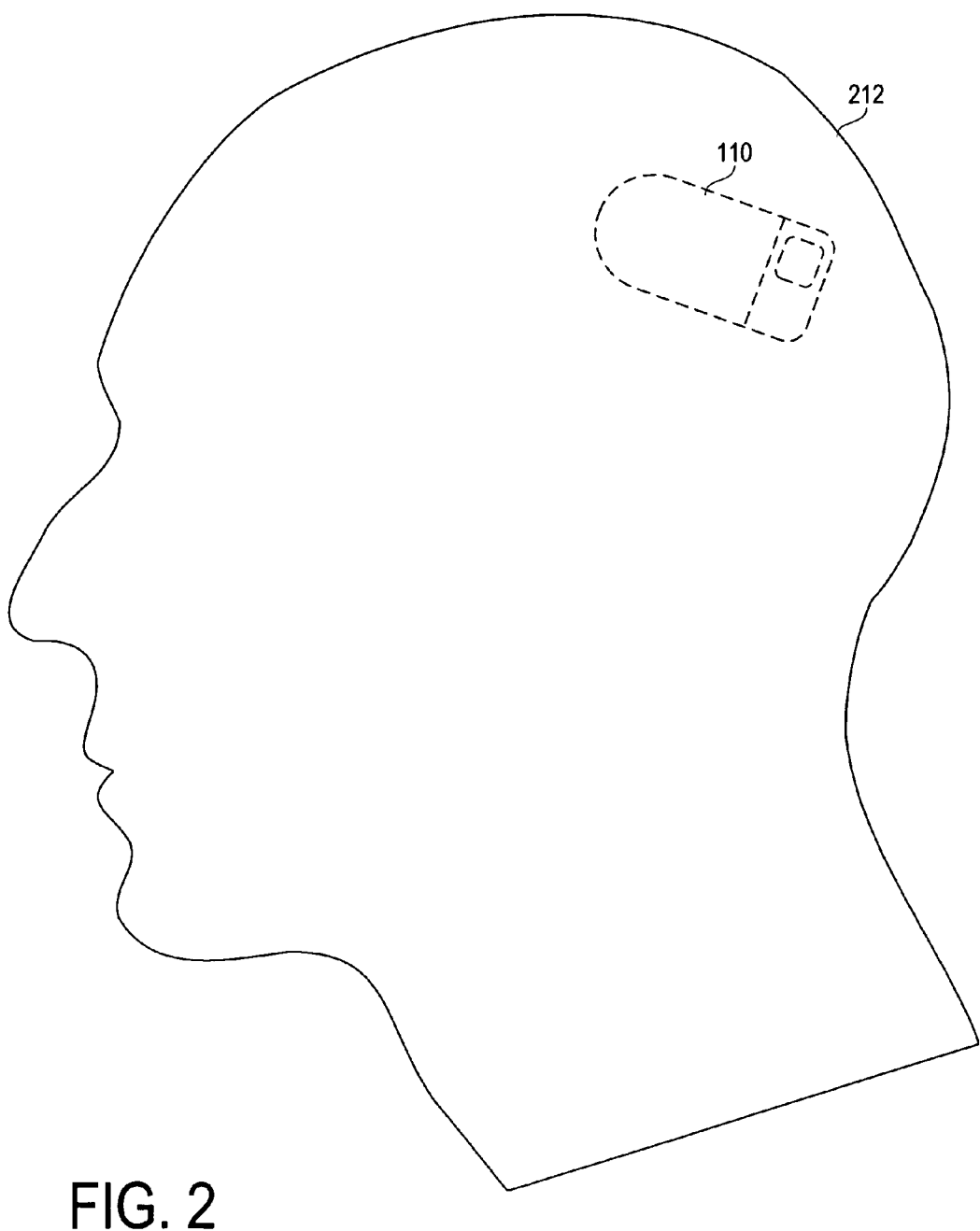
FIG. 2 is a schematic illustration of a patient's head showing the placement of an implantable neurostimulator according to an embodiment of the invention.

FIG. 2 depicts an intracranial implantation of the device 110 according to the invention, which in one embodiment is a small self-contained responsive neurostimulator. As the term is used herein, a responsive neurostimulator is a device capable of detecting or predicting neurological events, such as abnormal electrical activity, and providing electrical stimulation to neural tissue in response to that activity, where the electrical stimulation is specifically intended to terminate the abnormal activity, treat a neurological event, prevent an unwanted neurological event from occurring, or lessen the severity or frequency of certain symptoms of a neurological disorder. As disclosed herein, the responsive neurostimulator detects abnormal neurological activity by systems and methods according to the invention.

Preferably, an implantable device according to the invention is capable of detecting or predicting any kind of neurological event that has a representative electrographic signature. While the disclosed embodiment is described primarily as responsive to symptoms and conditions present in psychiatric disorders, it should be recognized that it is also possible to respond to other types of neurological disorders, such as epilepsy, movement disorders (e.g. the tremors characterizing Parkinson's disease), migraine headaches, and chronic pain. Preferably, neurological events representing any or all of these afflictions can be detected when they are actually occurring, in an onset stage, or as a predictive precursor before clinical symptoms begin.

Figure 3:
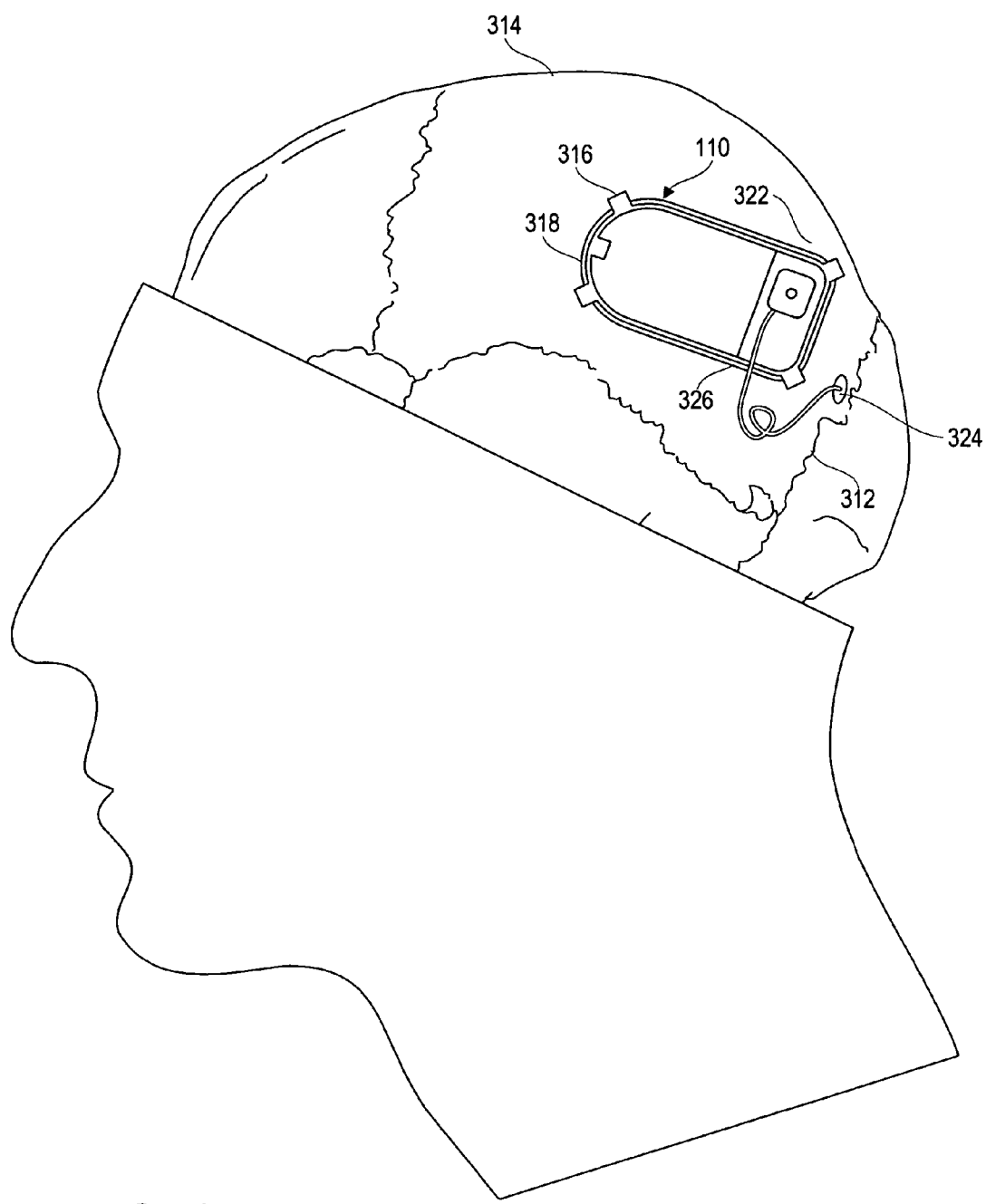
FIG. 3 is a schematic illustration of a patient's cranium showing the implantable neurostimulator of FIG. 2 as implanted, including a lead extending to the patient's brain.

In the disclosed embodiment, the neurostimulator is implanted intracranially in a patient's parietal bone 310, in a location anterior to the lambdoid suture 312 (see FIG. 3). It should be noted, however, that the placement described and illustrated herein is merely exemplary, and other locations and configurations are also possible, in the cranium or elsewhere, depending on the size and shape of the device and individual patient needs, among other factors. The device 110 is preferably configured to fit the contours of the patient's cranium 314. In an alternative embodiment, the device 110 is implanted under the patient's scalp 212 but external to the cranium; it is expected, however, that this configuration would generally cause an undesirable protrusion in the patient's scalp where the device is located. In yet another alternative embodiment, when it is not possible to implant the device intracranially, it may be implanted pectorally (not shown), with leads extending through the patient's neck and between the patient's cranium and scalp, as necessary.

It should be recognized that the embodiment of the device 110 described and illustrated herein is preferably a responsive neurostimulator for detecting and treating various psychiatric disorders and related disorders by detecting neurophysiological conditions, symptoms, or their onsets or precursors, and preventing and/or relieving such conditions and symptoms.

In an alternative embodiment of the invention, the device 110 is not a responsive neurostimulator, but is an apparatus capable of detecting neurological conditions and events and performing actions in response thereto. The actions performed by such an embodiment of the device 110 need not be therapeutic, but may involve data recording or transmission, providing warnings to the patient, or any of a number of known alternative actions. Such a device will typically act as a diagnostic device when interfaced with external equipment, as will be discussed in further detail below.

The device 110, as implanted intracranially, is illustrated in greater detail in FIG. 3. The device 110 is affixed in the patient's cranium 314 by way of a ferrule 316. The ferrule 316 is a structural member adapted to fit into a cranial opening, attach to the cranium 314, and retain the device 110.

To implant the device 110, a craniotomy is performed in the parietal bone 310 anterior to the lambdoid suture 312 to define an opening 318 slightly larger than the device 110. The ferrule 316 is inserted into the opening 318 and affixed to the cranium 314, ensuring a tight and secure fit. The device 110 is then inserted into and affixed to the ferrule 316.

As shown in FIG. 3, the device 110 includes a lead connector 320 adapted to receive one or more electrical leads, such as a first lead 322. The lead connector 320 acts to physically secure the lead 322 to the device 110, and facilitates electrical connection between a conductor in the lead 322 coupling an electrode to circuitry within the device 110. The lead connector 320 accomplishes this in a substantially fluid-tight environment with biocompatible materials.

The lead 322, as illustrated, and other leads for use in a system or method according to the invention, is a flexible elongated member having one or more conductors. As shown, the lead 322 is coupled to the device 110 via the lead connector 320, and is generally situated on the outer surface of the cranium 314 (and under the patient's scalp 212), extending between the device 110 and a burr hole 324 or other cranial opening, where the lead 322 enters the cranium 314 and is coupled to a depth electrode (e.g., one of the sensors 512-518 of FIG. 5) implanted in a desired location in the patient's brain. If the length of the lead 322 is substantially greater than the distance between the device 110 and the burr hole 324, any excess may be urged into a coil configuration under the scalp 212. As described in U.S. Pat. No. 6,006,124 to Fischell, et al., which is hereby incorporated by reference as though set forth in full herein, the burr hole 324 is sealed after implantation to prevent further movement of the lead 322; in an embodiment of the invention, a burr hole cover apparatus is affixed to the cranium 314 at least partially within the burr hole 324 to provide this functionality.

The device 110 includes a durable outer housing 326 fabricated from a biocompatible material. Titanium, which is light, extremely strong, and biocompatible, is used in analogous devices, such as cardiac pacemakers, and would serve advantageously in this context. As the device 110 is self-contained, the housing 326 encloses a battery and any electronic circuitry necessary or desirable to provide the functionality described herein, as well as any other features. As will be described in further detail below, a telemetry coil may be in the interior of the device 110 or provided outside of the housing 326 (and potentially integrated with the lead connector 320) to facilitate communication between the device 110 and external devices.

The neurostimulator configuration described herein and illustrated in FIG. 3 provides several advantages over alternative designs. First, the self-contained nature of the neurostimulator substantially decreases the need for access to the device 110, allowing the patient to participate in normal life activities. Its small size and intracranial placement causes a minimum of cosmetic disfigurement. The device 110 will fit in an opening in the patient's cranium, under the patient's scalp, with little noticeable protrusion or bulge. The ferrule 316 used for implantation allows the craniotomy to be performed and fit verified without the possibility of breaking the device 110, and also provides protection against the device 110 being pushed into the brain under external pressure or impact. A further advantage is that the ferrule 316 receives any cranial bone growth, so at explant, the device 110 can be replaced without removing any bone screws—only the fasteners retaining the device 110 in the ferrule 316 need be manipulated.

Figure 4:
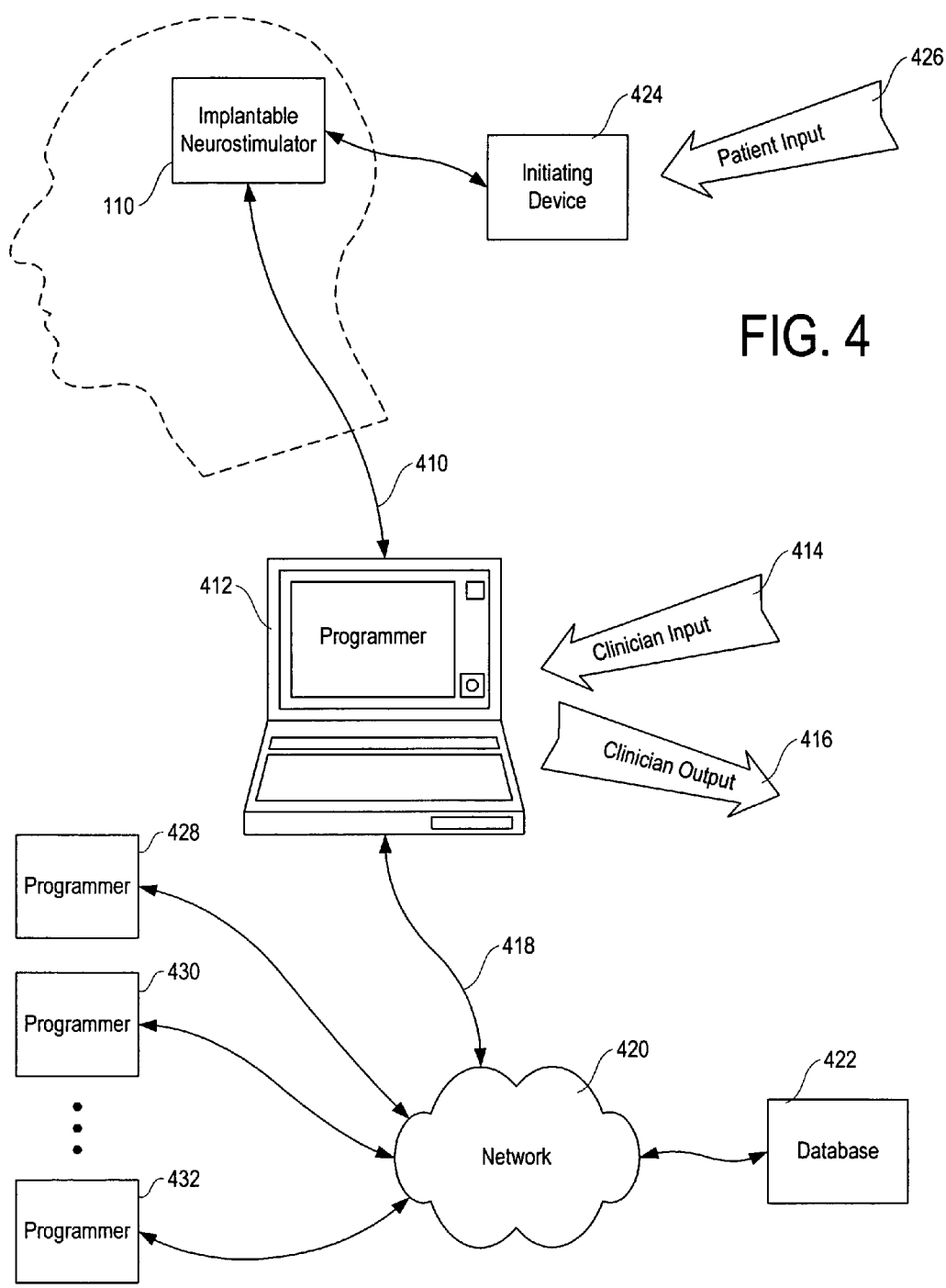
FIG. 4 is a block diagram illustrating a system context in which an implantable neurostimulator according to the invention is implanted and operated.

As stated above, and as illustrated in FIG. 4, a neurostimulator according to the invention operates in conjunction with external equipment. The implantable neurostimulator device 110 is mostly autonomous (particularly when performing its usual sensing, detection, and stimulation capabilities), but preferably includes a selectable part-time wireless link 410 to external equipment such as a programmer 412. In the disclosed embodiment of the invention, the wireless link 410 is established by moving a wand (or other apparatus) having communication capabilities and coupled to the programmer 412 into communication range of the implantable neurostimulator device 110. The programmer 412 can then be used to manually control the operation of the device, as well as to transmit information to or receive information from the implantable neurostimulator 110. Several specific capabilities and operations performed by the programmer 412 in conjunction with the device will be described in further detail below.

The programmer 412 is capable of performing a number of advantageous operations in connection with the invention. In particular, the programmer 412 is able to specify and set variable parameters in the implantable neurostimulator device 110 to adapt the function of the device to meet the patient's needs, upload or receive data (including but not limited to stored EEG waveforms, parameters, or logs of actions taken) from the implantable neurostimulator 110 to the programmer 412, download or transmit program code and other information from the programmer 412 to the implantable neurostimulator 110, or command the implantable neurostimulator 110 to perform specific actions or change modes as desired by a physician operating the programmer 412. To facilitate these functions, the programmer 412 is adapted to receive clinician input 414 and provide clinician output 416; data is transmitted between the programmer 412 and the implantable neurostimulator 110 over the wireless link 410.

The programmer 412 may be used at a location remote from the implantable neurostimulator 110 if the wireless link 410 is enabled to transmit data over long distances. For example, the wireless link 410 may be established by a short-distance first link between the implantable neurostimulator 110 and a transceiver, with the transceiver enabled to relay communications over long distances to a remote programmer 412, either wirelessly (for example, over a wireless computer network) or via a wired communications link (such as a telephonic circuit or a computer network).

The programmer 412 may also be coupled via a communication link 418 to a network 420 such as the Internet. This allows any information uploaded from the implantable neurostimulator 110, as well as any program code or other information to be downloaded to the implantable neurostimulator 110, to be stored in a database 422 at one or more data repository locations (which may include various servers and network-connected programmers like the programmer 412). This would allow a patient (and the patient's physician) to have access to important data, including past treatment information and software updates, essentially anywhere in the world where there is a programmer (like the programmer 412) and a network connection. Alternatively, the programmer 412 may be connected to the database 422 over a trans-telephonic link.

In yet another alternative embodiment of the invention, the wireless link 410 from the implantable neurostimulator 110 may enable a transfer of data from the neurostimulator 110 to the database 422 without any involvement by the programmer 412. In this embodiment, as with others, the wireless link 410 may be established by a short-distance first link between the implantable neurostimulator 110 and a transceiver, with the transceiver enabled to relay communications over long distances to the database 422, either wirelessly (for example, over a wireless computer network) or via a wired communications link (such as trans-telephonically over a telephonic circuit, or over a computer network).

In the disclosed embodiment, the implantable neurostimulator 110 is also adapted to receive communications from an initiating device 424, typically controlled by the patient or a caregiver. Accordingly, patient input 426 from the initiating device 424 is transmitted over a wireless link to the implantable neurostimulator 110; such patient input 426 may be used to cause the implantable neurostimulator 110 to switch modes (on to off and vice versa, for example) or perform an action (e.g., store a record of EEG data). Preferably, the initiating device 424 is able to communicate with the implantable neurostimulator 110 through a communication subsystem 530 (FIG. 5), and possibly in the same manner the programmer 412 does. The link may be unidirectional (as with the magnet and GMR sensor described below), allowing commands to be passed in a single direction from the initiating device 424 to the implantable neurostimulator 110, but in an alternative embodiment of the invention is bi-directional, allowing status and data to be passed back to the initiating device 424. Accordingly, the initiating device 424 may be a programmable PDA or other hand-held computing device, such as a Palm® device or PocketPC®. However, a simple form of initiating device 424 may take the form of a permanent magnet, if the communication subsystem 530 (FIG. 5) is adapted to identify magnetic fields and interruptions therein as communication signals.

The implantable neurostimulator 110 (FIG. 1) generally interacts with the programmer 412 (FIG. 4) as described below. Data stored in a memory subsystem 526 (FIG. 5) of the device 110 can be retrieved by the patient's physician through the wireless communication link 410, which operates through the communication subsystem 530 of the implantable neurostimulator 110. In connection with the invention, a software operating program run by the programmer 412 allows the physician to read out a history of neurological events detected including EEG information before, during, and after each neurological event, as well as specific information relating to the detection of each neurological event (such as, in one embodiment, the time-evolving energy spectrum of the patient's EEG). The programmer 412 also allows the physician to specify or alter any programmable parameters of the implantable neurostimulator 110. The software operating program also includes tools for the analysis and processing of recorded EEG records to assist the physician in developing optimized seizure detection parameters for each specific patient.

In an embodiment of the invention, the programmer 412 is primarily a commercially available PC, laptop computer, or workstation having a CPU, keyboard, mouse and display, and running a standard operating system such as Microsoft Windows®, Linux®, Unix®, or Apple Mac OS®. It is also envisioned that a dedicated programmer apparatus with a custom software package (which may not use a standard operating system) could be developed.

When running the computer workstation software operating program, the programmer 412 can process, store, play back and display on the display the patient's EEG signals, as previously stored by the implantable neurostimulator 110 of the implantable neurostimulator device.

The computer workstation software operating program also has the capability to simulate the detection and prediction of abnormal electrical activity and other symptoms of psychiatric disorders. Furthermore, the software operating program of the present invention has the capability to allow a clinician to create or modify a patient-specific collection of information comprising, in one embodiment, algorithms and algorithm parameters for specific activity detection. The patient-specific collection of detection algorithms and parameters used for neurological activity detection according to the invention will be referred to herein as a detection template or patient-specific template. The patient-specific template, in conjunction with other information and parameters generally transferred from the programmer to the implanted device (such as stimulation parameters, time schedules, and other patient-specific information), make up a set of operational parameters for the neurostimulator.

Following the development of a patient specific template on the programmer 412, the patient-specific template would be downloaded through the communications link 410 from the programmer 412 to the implantable neurostimulator 110.

The patient-specific template is used by a detection subsystem 522 and CPU 528 (FIG. 5) of the implantable neurostimulator 110 to detect conditions indicating treatment should be administered, and can be programmed by a clinician to result in responsive stimulation of the patient's brain, as well as the storage of EEG records before and after the detection, facilitating later clinician review.

Preferably, the database 422 is adapted to communicate over the network 420 with multiple programmers, including the programmer 412 and additional programmers 428, 430, and 432. It is contemplated that programmers will be located at various medical facilities and physicians' offices at widely distributed locations. Accordingly, if more than one programmer has been used to upload EEG records from a patient's implantable neurostimulator 110, the EEG records will be aggregated via the database 422 and available thereafter to any of the programmers connected to the network 420, including the programmer 412.

Figure 5:
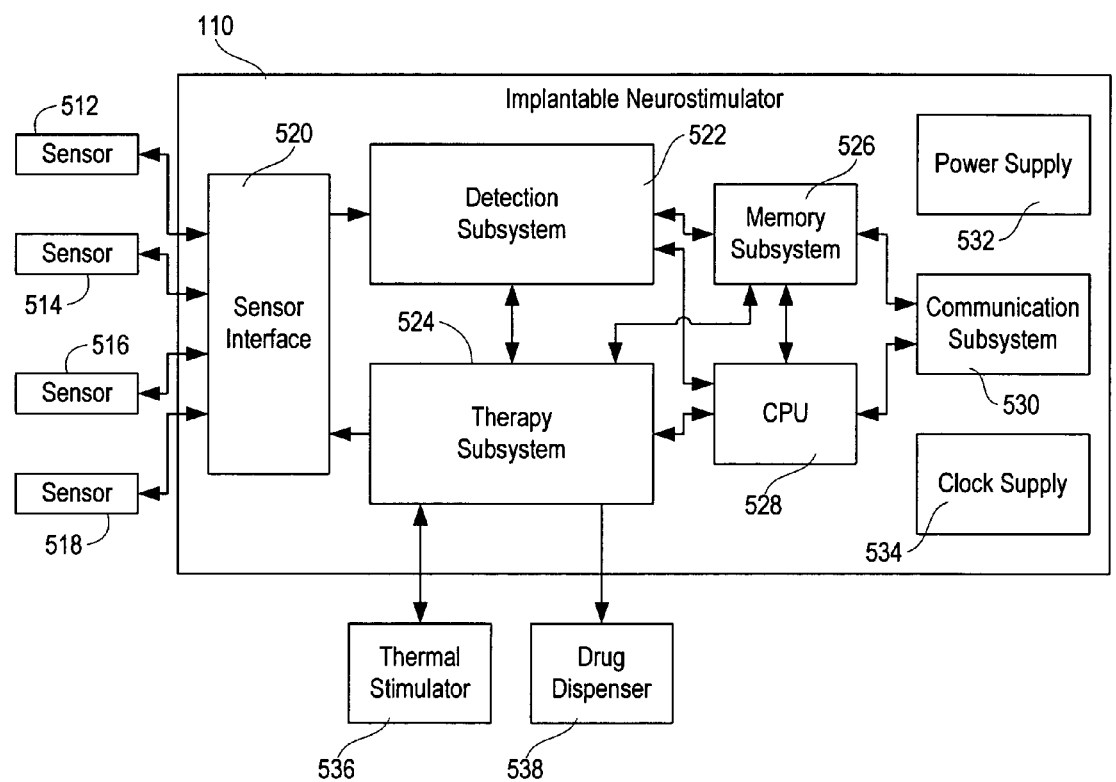
FIG. 5 is a block diagram illustrating the major functional subsystems of an implantable neurostimulator according to the invention.

FIG. 5 is an overall block diagram of the implantable neurostimulator device 110 used for measurement, detection, and treatment according to the invention. Inside the housing of the neurostimulator device 110 are several subsystems making up the device. The implantable neurostimulator device 110 is capable of being coupled to a plurality of sensors 512, 514, 516, and 518 (each of which may be individually or together connected to the implantable neurostimulator device 110 via one or more leads), which in an embodiment of the invention are electrodes used for both sensing and stimulation as well as the delivery of other treatment modalities. In the illustrated embodiment, the coupling is accomplished through a lead connector. Although four sensors are shown in FIG. 5, it should be recognized that any number is possible, and in the embodiment described in detail below, eight electrodes are used as sensors. In fact, it is possible to employ an embodiment of the invention that uses a single lead with at least two electrodes, or two leads each with a single electrode (or with a second electrode provided by a conductive exterior portion of the housing in one embodiment), although bipolar sensing between two closely spaced electrodes on a lead is preferred to minimize common mode signals including noise.

The sensors 512-518 are in contact with the patient's brain or are otherwise advantageously located to receive EEG signals or provide electrical stimulation or another therapeutic modality. Each of the sensors 512-518 is also electrically coupled to a sensor interface 520. Preferably, the electrode interface is capable of selecting each electrode as required for sensing and stimulation; accordingly the electrode interface is coupled to a detection subsystem 522 and a therapy subsystem 524 (which, in various embodiments of the invention, may provide electrical stimulation and other therapies). The sensor interface 520 may also provide any other features, capabilities, or aspects, including but not limited to amplification, isolation, and charge-balancing functions, that are required for a proper interface with neurological tissue and not provided by any other subsystem of the device 110.

In an embodiment of the invention in which electrographic signals are received by electrodes and analyzed, the detection subsystem 522 includes and serves primarily as an EEG waveform analyzer. It will be recognized that similar principles apply to the analysis of other types of waveforms received from other types of sensors. Detection is generally accomplished in conjunction with a central processing unit (CPU) 528. The waveform analyzer function is adapted to receive signals from the sensors 512-518, through the sensor interface 520, and to process those EEG signals to identify abnormal neurological activity characteristic of a disease or symptom thereof. One way to implement such EEG analysis functionality is disclosed in detail in U.S. Pat. No. 6,016,449 to Fischell et al., incorporated by reference above. Additional inventive methods are described in U.S. Pat. No. 6,810,285 to Pless et al., filed on Jun. 28, 2001, issued Oct. 26, 2004, and entitled "SEIZURE SENSING AND DETECTION USING AN IMPLANTABLE DEVICE," of which relevant details will be set forth below (and which is also incorporated by reference as though set forth in full). The detection subsystem may optionally also contain further sensing and detection capabilities, including but not limited to parameters derived from other physiological conditions (such as electrophysiological parameters, temperature, blood pressure, neurochemical concentration, etc.). In general, prior to analysis, the detection subsystem performs amplification, analog-to-digital conversion, and multiplexing functions on the signals in the sensing channels received from the sensors 512-518.

The therapy subsystem 524 is capable of applying electrical stimulation or other therapies to neurological tissue. This can be accomplished in any of a number of different manners. For example, it may be advantageous in some circumstances to provide stimulation in the form of a substantially continuous stream of pulses, or on a scheduled basis. Preferably, therapeutic stimulation is provided in response to abnormal neurological events or conditions detected by the waveform analyzer function of the detection subsystem 522. As illustrated in FIG. 5, the therapy subsystem 524 and the EEG analyzer function of the detection subsystem 522 are in communication; this facilitates the ability of therapy subsystem 524 to provide responsive electrical stimulation and other therapies, as well as an ability of the detection subsystem 522 to blank the amplifiers while electrical stimulation is being performed to minimize stimulation artifacts. It is contemplated that the parameters of a stimulation signal (e.g., frequency, duration, waveform) provided by the therapy subsystem 524 would be specified by other subsystems in the implantable device 110, as will be described in further detail below.

In accordance with the invention, the therapy subsystem 524 may also provide for other types of stimulation, besides electrical stimulation described above. In particular, in certain circumstances, it may be advantageous to provide audio, visual, or tactile signals to the patient, to provide somatosensory electrical stimulation to locations other than the brain, or to deliver a drug or other therapeutic agent (either alone or in conjunction with stimulation).

Also the implantable neurostimulator device 110 contains a memory subsystem 526 and the CPU 528, which can take the form of a microcontroller. The memory subsystem is coupled to the detection subsystem 522 (e.g., for receiving and storing data representative of sensed EEG or other signals and evoked responses), the therapy subsystem 524 (e.g., for providing stimulation waveform parameters to the therapy subsystem for electrical stimulation), and the CPU 528, which can control the operation of (and store and retrieve data from) the memory subsystem 526. In addition to the memory subsystem 526, the CPU 528 is also connected to the detection subsystem 522 and the therapy subsystem 524 for direct control of those subsystems.

Also provided in the implantable neurostimulator device 110, and coupled to the memory subsystem 526 and the CPU 528, is a communication subsystem 530. The communication subsystem 530 enables communication between the device 110 and the outside world, particularly an external programmer 412 and a patient initiating device 424, both of which are described above with reference to FIG. 4. As set forth above, the disclosed embodiment of the communication subsystem 530 includes a telemetry coil (which may be situated inside or outside of the housing of the implantable neurostimulator device 110) enabling transmission and reception of signals, to or from an external apparatus, via inductive coupling. Alternative embodiments of the communication subsystem 530 could use an antenna for an RF link or an audio transducer for an audio link. Preferably, the communication subsystem 530 also includes a GMR (giant magnetoresistive effect) sensor to enable receiving simple signals (namely the placement and removal of a magnet) from a patient initiating device; this capability can be used to initiate signal recording as will be described in further detail below.

If the therapy subsystem 524 includes the audio capability set forth above, it may be advantageous for the communication subsystem 530 to cause the audio signal to be generated by the therapy subsystem 524 upon receipt of an appropriate indication from the patient initiating device (e.g., the magnet used to communicate with the GMR sensor of the communication subsystem 530), thereby confirming to the patient or caregiver that a desired action will be performed, e.g. that an EEG record will be stored.

Several support components are present in the implantable neurostimulator device 110, including a power supply 532 and a clock supply 534. The power supply 532 supplies the voltages and currents necessary for each of the other subsystems. The clock supply 534 supplies substantially all of the other subsystems with any clock and timing signals necessary for their operation, including a real-time clock signal to coordinate programmed and scheduled actions and the timer functionality used by the detection subsystem 522 that is described in detail below.

In an embodiment of the invention, the therapy subsystem 524 is coupled to a thermal stimulator 536 and a drug dispenser 538, thereby enabling therapy modalities other than electrical stimulation. These additional treatment modalities will be discussed further below. Any of the therapies delivered by the therapy subsystem 524 is delivered to a therapy output at a specific site; it will be recognized that the therapy output may be a stimulation electrode, a drug dispenser outlet, or a thermal stimulation site (e.g. Peltier junction or thermocouple) as appropriate for the selected modality.

It should be observed that while the memory subsystem 526 is illustrated in FIG. 5 as a separate functional subsystem, the other subsystems may also require various amounts of memory to perform the functions described above and others. Furthermore, while the implantable neurostimulator device 110 is preferably a single physical unit (i.e., a control module) contained within a single implantable physical enclosure, namely the housing described above, other embodiments of the invention might be configured differently. The neurostimulator 110 may be provided as an external unit not adapted for implantation, or it may comprise a plurality of spatially separate units each performing a subset of the capabilities described above, some or all of which might be external devices not suitable for implantation. Also, it should be noted that the various functions and capabilities of the subsystems described above may be performed by electronic hardware, computer software (or firmware), or a combination thereof. The division of work between the CPU 528 and the other functional subsystems may also vary—the functional distinctions illustrated in FIG. 5 may not reflect the partitioning and integration of functions in a real-world system or method according to the invention.

Figure 6:
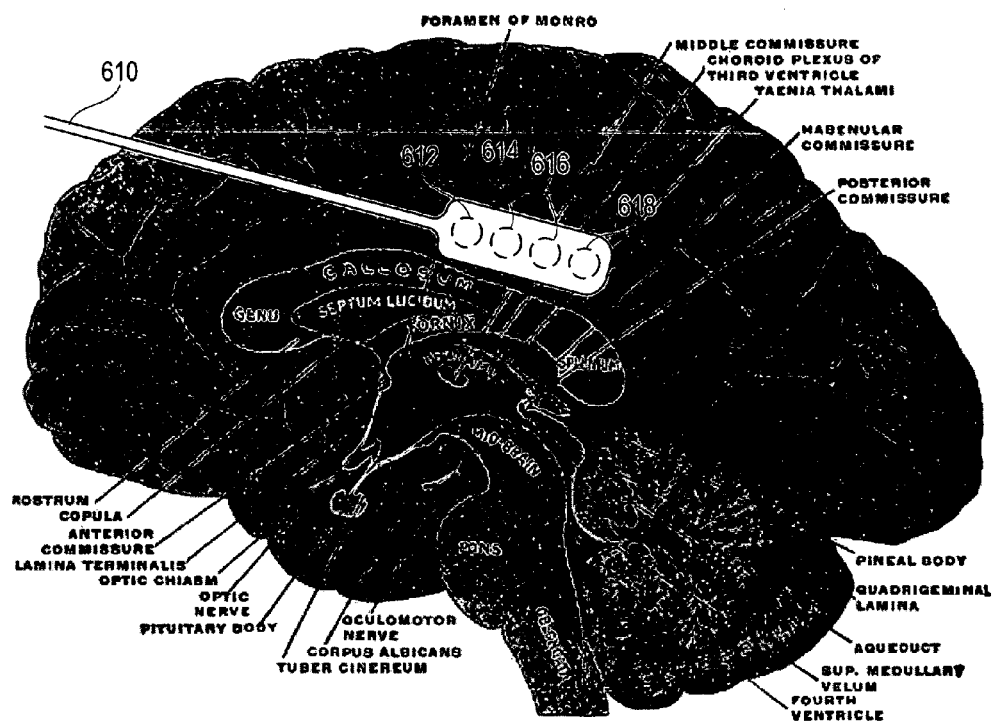
FIG. 6 is a drawing of an exemplary brain hemisphere and an exemplary cortical electrode positioned over the cingulate gyrus.

FIG. 6 depicts the previously illustrated hemisphere of a patient's brain 112 with a distal end of an exemplary cortical lead 610 positioned thereupon. In the illustrated embodiment, the cortical lead 610 approaches the cingulate cortex 114 from a generally anterior direction; the lead 610 interfaces with the neurostimulator device 110 (FIG. 1) at its proximal end (not shown). The cortical lead may also be implanted from different approaches, depending on the surgeon's preference. The distal end of the cortical lead 610 bears four disc electrodes 612-618, each of which is in contact with or in close proximity to the surface of the cingulate gyrus 114. The entirety of the exemplary cortical lead is formed from biocompatible materials such as silicone and platinum.

Figure 7:
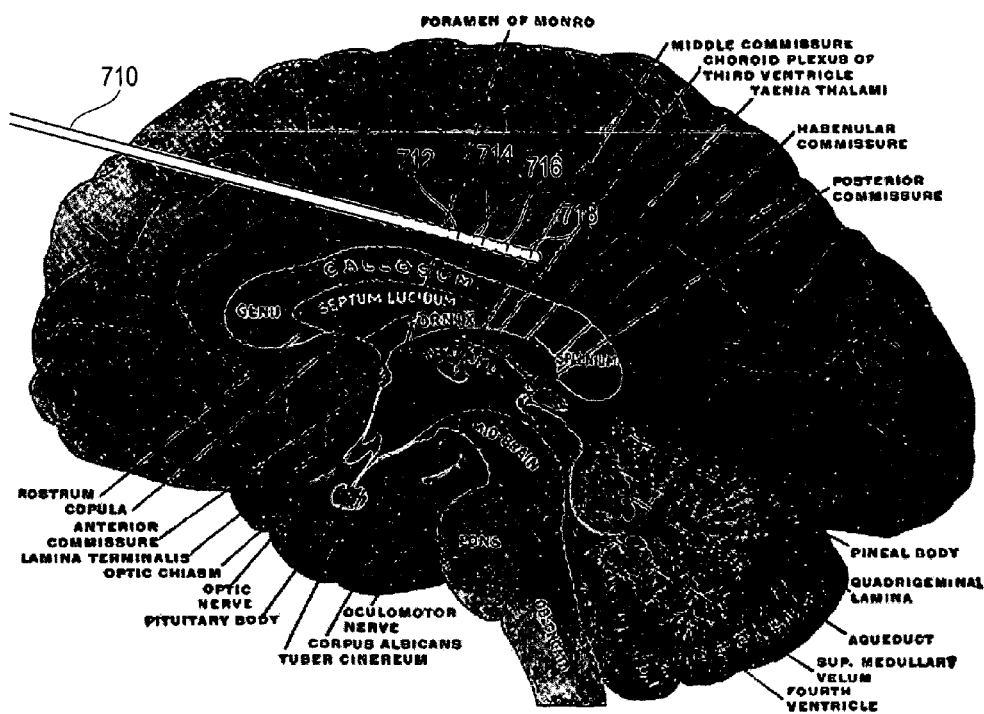
FIG. 7 is a drawing of an exemplary brain hemisphere and an exemplary depth electrode positioned in the cingulate gyrus.

FIG. 7 depicts the previously illustrated hemisphere of a patient's brain 112 with a distal end of an exemplary depth lead 710 implanted therein. In the illustrated embodiment, the depth lead 710 interfaces with the neurostimulator device 110 (FIG. 1) at its proximal end (not shown). The distal end of the depth lead 710 bears four ring electrodes 712-718 preferably implanted into the gray matter of the cingulate gyrus 114. As with the cortical lead 610, the depth lead 710 is fabricated from biocompatible materials.

In the disclosed embodiment of the invention, the neurostimulator device 110 is capable of receiving two leads, each with four electrodes. One cortical lead 610 and one depth lead 710, two cortical leads, or two depth leads can be used simultaneously to achieve the desired coverage of the cingulate gyrus 114 or other desired brain areas. It will be recognized that other embodiments of a system according to the invention may receive more leads, or leads and sensors in different forms than those specifically disclosed herein.

Figure 8:
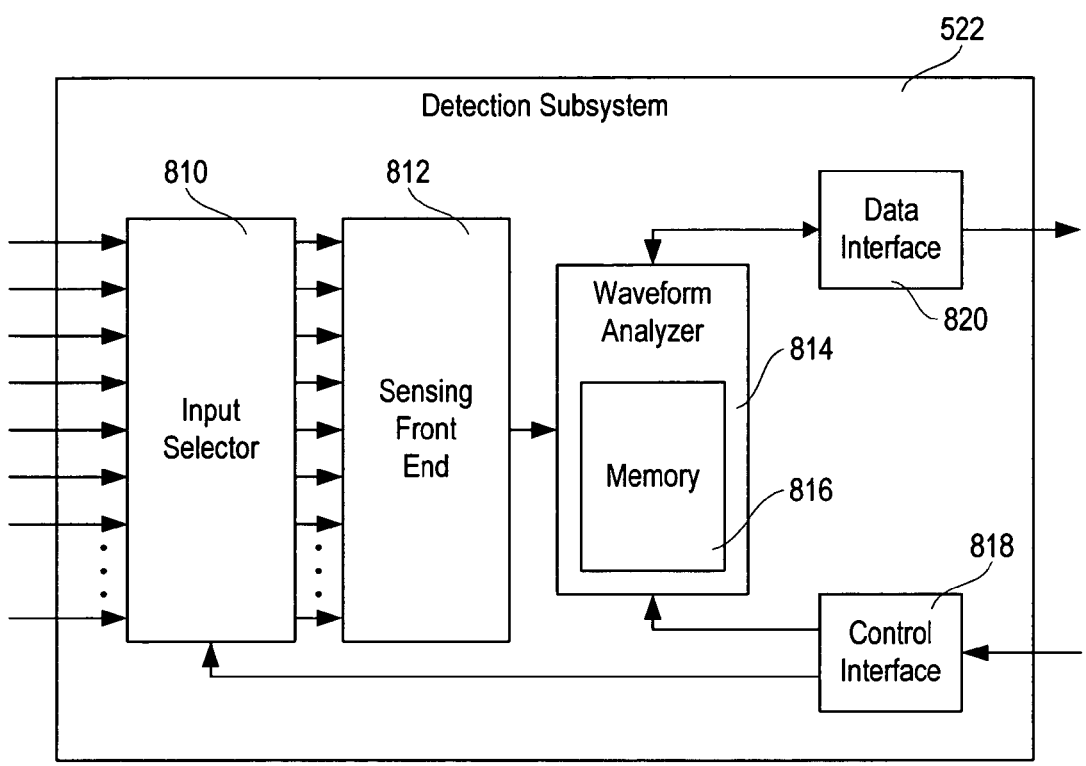
FIG. 8 is a block diagram illustrating the functional components of the detection subsystem of the implantable neurostimulator shown in FIG. 5.

FIG. 8 illustrates details of the detection subsystem 52 (FIG. 5). Inputs from the electrodes 512-518 are on the left, and connections to other subsystems are on the right.

Signals received from the sensors 512-518 (as routed through the sensor interface 520) are received in an input selector 810. The input selector 810 allows the device to select which electrodes or other sensors (of the sensors 512-518) should be routed to which individual sensing channels of the detection subsystem 522, based on commands received through a control interface 818 from the memory subsystem 526 or the CPU 528 (FIG. 5). Preferably, when electrodes are used for sensing, each sensing channel of the detection subsystem 522 receives a bipolar signal representative of the difference in electrical potential between two selectable electrodes. Accordingly, the input selector 810 provides signals corresponding to each pair of selected electrodes to a sensing front end 812, which performs amplification, analog to digital conversion, and multiplexing functions on the signals in the sensing channels.

A multiplexed input signal representative of all active sensing channels is then fed from the sensing front end 812 to a waveform analyzer 814. The waveform analyzer 814 is preferably a special-purpose digital signal processor (DSP) adapted for use with the invention, or in an alternative embodiment, may comprise a programmable general-purpose DSP. In the disclosed embodiment, the waveform analyzer has its own scratchpad memory area 816 used for local storage of data and program variables when the signal processing is being performed. In either case, the signal processor performs suitable measurement and detection methods described generally above and in greater detail below. Any results from such methods, as well as any digitized signals intended for storage transmission to external equipment, are passed to various other subsystems of the device 110, including the memory subsystem 526 and the CPU 528 (FIG. 5) through a data interface 820. Similarly, the control interface 818 allows the waveform analyzer 814 and the input selector 810 to be in communication with the CPU 528. The waveform analyzer 714 is illustrated in detail in FIG. 9.

Figure 9:
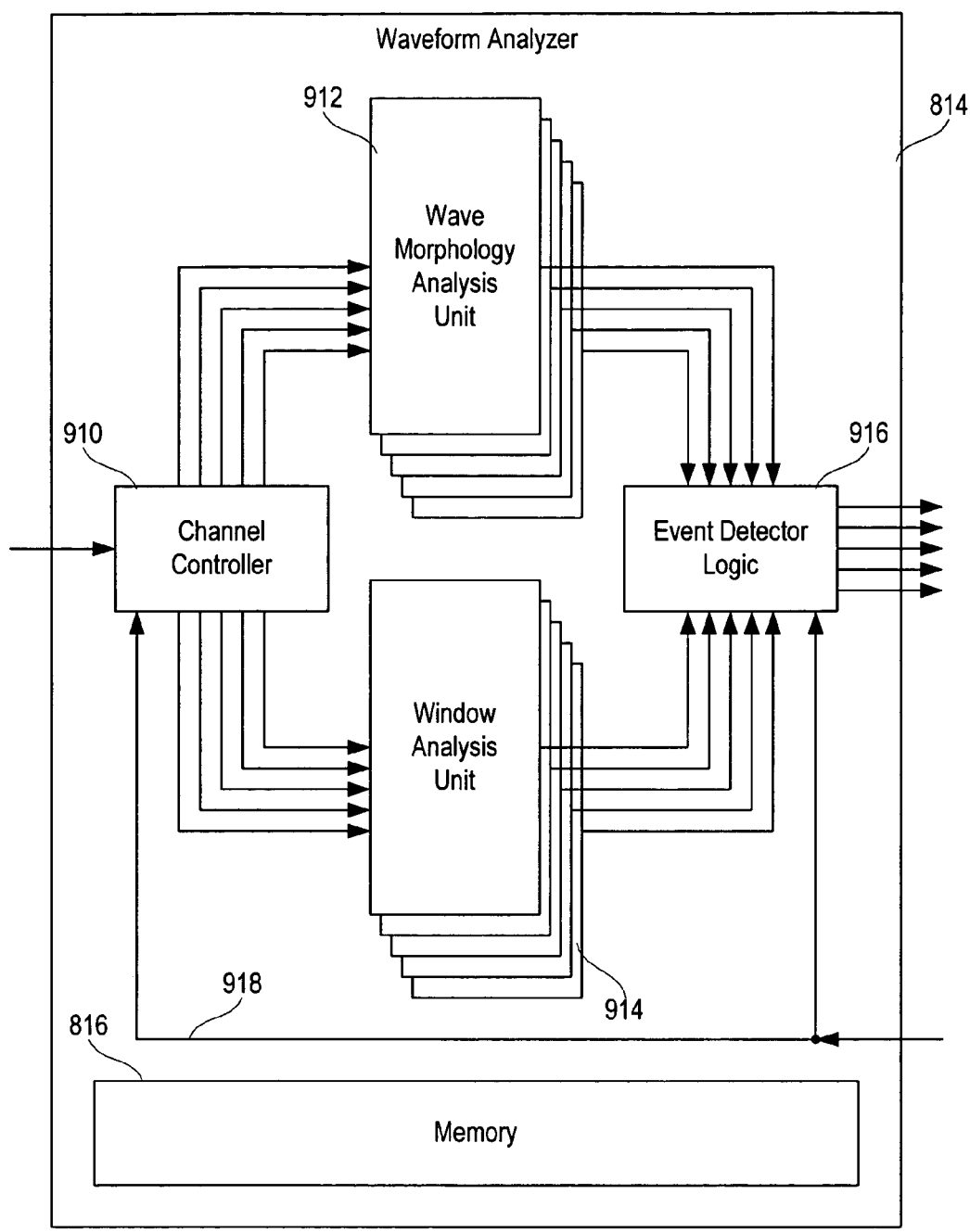
FIG. 9 is a block diagram illustrating the components of the waveform analyzer of the detection subsystem of FIG. 8.

In the exemplary waveform analyzer illustrated in FIG. 9, the interleaved digital data stream representing information from all of the active sensing channels is first received by a channel controller 910. The channel controller applies information from the active sensing channels to a number of wave morphology analysis units 912 and window analysis units 914. It is preferred to have as many wave morphology analysis units 912 and window analysis units 914 as possible, consistent with the goals of efficiency, size, and low power consumption necessary for an implantable device. In a presently preferred embodiment of the invention, there are sixteen wave morphology analysis units 912 and eight window analysis units 914, each of which can receive data from any of the sensing channels of the sensing front end 812 (FIG. 8), and each of which can be operated with different and independent parameters, including differing sample rates, as will be discussed in further detail below.

Each of the wave morphology analysis units 912 operates to extract certain feature information from an input waveform. Similarly, each of the window analysis units 914 performs certain data reduction and signal analysis within time windows. Output data from the various wave morphology analysis units 912 and window analysis units 914 are combined via event detector logic 916. The event detector logic 916 and the channel controller 910 are controlled by control commands 918 received from the control interface 818 (FIG. 8).

A "detection channel," as the term is used herein, refers to a data stream including the active sensing front end 812 and the analysis units of the waveform analyzer 814 processing that data stream, in both analog and digital forms. It should be noted that each detection channel can receive data from a single sensing channel; each sensing channel preferably can be applied to the input of any combination of detection channels. The latter selection is accomplished by the channel controller 910. As with the sensing channels, not all detection channels need to be active; certain detection channels can be deactivated to save power or if additional detection processing is deemed unnecessary in certain applications.

In conjunction with the operation of the wave morphology analysis units 912 and the window analysis units 914, a scratchpad memory area 816 is provided for temporary storage of processed data. The scratchpad memory area 816 may be physically part of the memory subsystem 526 (FIG. 5), or alternatively may be provided for the exclusive use of the waveform analyzer 814 (FIG. 8). Other subsystems and components of a system according to the invention may also be furnished with local scratchpad memory, if such a configuration is advantageous.

A system according to the invention, particularly the neurostimulator device 110, is contemplated to be capable of multiple modalities of therapy. In general, regular or scheduled therapy may be considered advantageous at certain times, and may be scheduled to operate in parallel with responsive therapy modes. Moreover, the neurostimulator device 110 is also gathering data to enable therapy refinement in connection with the programmer 412 (FIG. 4) and other external equipment. This process is illustrated in more detail in connection with FIG. 10.

A scheduler process maintained by the hardware of the implantable neurostimulator device 110 (FIG. 1), typically in the CPU 528 (FIG. 5), allows multiple tasks to be performed by the neurostimulator device 110 in rapid sequence, effectively in parallel. In general, the scheduler allows subsidiary data collection, therapy delivery, and data analysis functions to be performed regularly. The scheduler is initially checked (step 1010). If it is time to collect data (step 1012)—as specified, generally, in a table of data collection times generated by the programmer 412 (FIG. 4)—then a record of data is collected (step 1014). Various types of sensor data, including electrographic signal waveforms, may be collected by a system according to the invention. If it is time to deliver an episode of scheduled therapy (step 1016), then therapy is delivered (step 1018). It should be noted that various types of therapy may be delivered, including but not limited to electrical stimulation and the administration of a dose of a therapeutic agent. As with data collection times, therapy times may be uploaded from the programmer 412 based on patient-specific observations made in the past or on some other desired dose schedule.

Inputs and other conditions are then observed (step 1020). A responsive therapy decision is made (step 1022) based on the conditions observed by the neurostimulator device 110, including but not limited to electrographic activity, brain chemistry, temperature, other indicia of physiological conditions and metabolic rate, and patient intent (as indicated by a signal received from the patient initiating device 424 (FIG. 4). Details on the conditions and information considered in a therapy decision are treated in more detail below with reference to FIGS. 11-17. If therapy is indicated, therapy is delivered (step 1024).

It should be noted that the scheduler function may also trigger other types of functions by the neurostimulator device 110, such as administrative functions. The nature of these additional functions would be understood by an engineer competent in designing real-time systems.

A number of lines of evidence identify the cingulate as a key region of the brain involved in major depression. Functional and structural brain neuroimaging in persons with major depressive disorder reveal abnormalities in the anterior cingulate cortex. Anterior cingulate cortex volume is reduced in persons with major depression as demonstrated by MRI and by post-mortem study. PET scans show reduced cingulate activation in depressed persons performing cognitive tasks. Such abnormalities improve with relief of symptoms and worsen with worsening symptoms.

These observations suggest that modulation of cingulate metabolism by electrical stimulation in a dynamic and responsive fashion could relieve depressive symptoms. Continuous recording of electrocorticographic activity or of other biological markers enables monitoring of disease state and can direct the therapeutic electrical stimulation. Changes in metabolic activity could prompt delivery of electrical stimulation that is determined by the direction of change—that is stimulation that is primarily excitatory can be applied when metabolism is inappropriately low and an inhibitory stimulation applied when metabolism is abnormally active. Stimulation can also be modified according to patient symptoms. Another advantage of this system is that applying stimulation only when the patient is symptomatic should extend battery life beyond the battery life of a system providing continuous stimulation.

Figure 11:
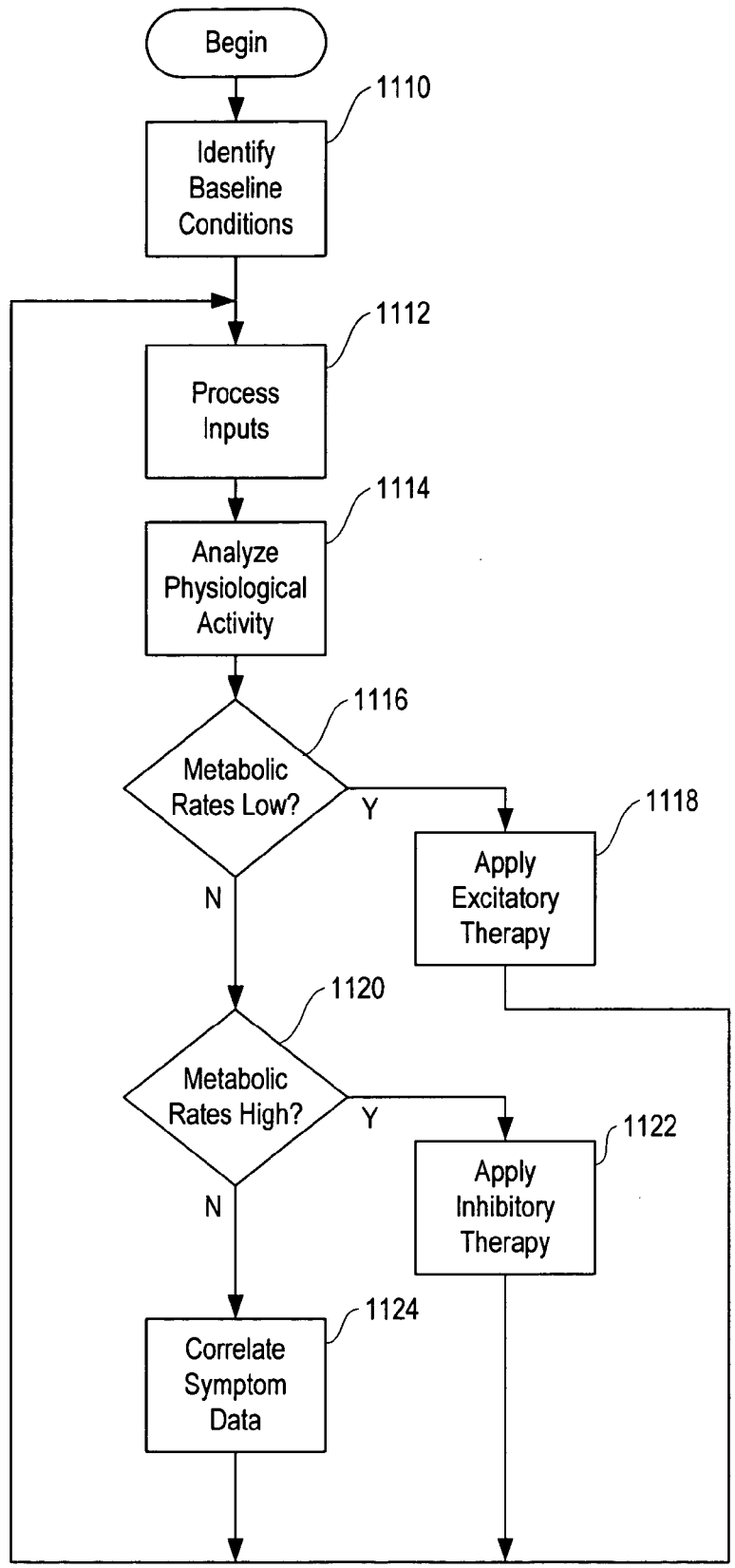
FIG. 11 is a flow chart illustrating a process advantageously used by a system according to the invention to treat major depression.

Referring now to FIG. 11, a specific method for treating depression begins by identifying baseline conditions (step 1110) in metabolic rates and electrographic activity. Ideally, this step is performed while the patient is feeling relatively symptom-free or when the patient is at his or her usual level of depression. A system according to the invention then receives inputs (step 1112) and analyzes physiological activity (step 1114). If the patient's metabolic rates, as determined by observing electrographic activity and other indicia of metabolic rate, are abnormally low (step 1116) in comparison to the baseline, excitatory therapy is applied (step 1118). Excitatory therapy may include electrical stimulation having excitatory characteristics (or applied to a pathway that tends to excite the target area) or the release of a therapeutic agent having excitatory effects. If the patient's metabolic rates are abnormally high (step 1120) in comparison to the baseline, inhibitory therapy is applied (step 1122). Inhibitory therapy may include electrical stimulation having inhibitory characteristics (or applied to a pathway that tends to inhibit the target area) or the release of a therapeutic agent having inhibitory effects.

Preferably, the method of treating depression includes the ability to correlate symptom data to observed inputs (step 1124). If the patient, using the initiating device 424 (FIG. 4) indicates that an episode of depression or an exacerbation of depressive symptoms is occurring, the neurostimulator device 110 can store a record of data to be analyzed either by the CPU 528 (FIG. 5) or offline by a programmer 412 (FIG. 4) or other device. Later observations of the same or similar data will then suggest an episode of depression, even when no patient input is received.

Bipolar disorder is associated with disturbances in attention, cognition and impulse regulation thought to be related to disturbances in the cingulate gyrus. There are structural abnormalities in the cingulate in persons with bipolar disorder, such as cellular and volumetric abnormalities. Functional MRI in persons with bipolar disorder shows differential activation in the cingulate depending upon whether the patient is depressed or is experiencing elevated mood.

Similar to major depression, these findings imply that metabolism, electrical activity, and neurochemicals vary with mood and that stimulation therapy applied to the cingulate will be most effective if it can be modified according to the patient's symptoms. Mood changes in persons with bipolar disorder may occur over months, weeks, days or even hours. Therefore, a responsive system with modifiable stimulation parameters would appear to be of great interest as a treatment for this disorder.

Figure 12:
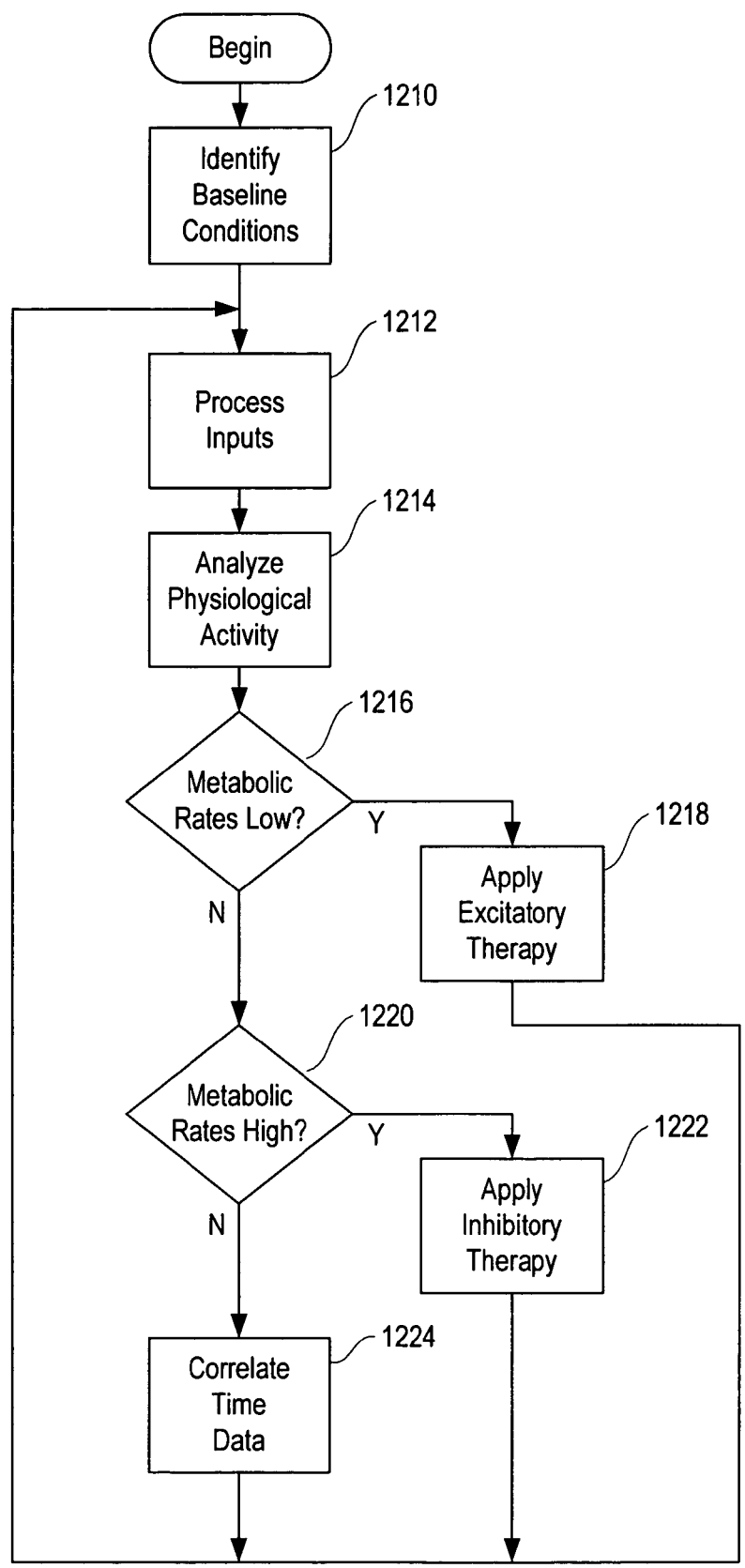
FIG. 12 is a flow chart illustrating a process advantageously used by a system according to the invention to treat bipolar disorder.

In FIG. 12, a specific method for treating bipolar disorder begins by identifying baseline conditions (step 1210) in metabolic rates and electrographic activity. Ideally, this step is performed while the patient is feeling relatively symptom-free or when the patient is at a known level of depression or mania. A system according to the invention then receives inputs (step 1212) and analyzes physiological activity (step 1214). If the patient's metabolic rates, as determined by observing electrographic activity and other indicia of metabolic rate, are abnormally low (step 1216) in comparison to the baseline, excitatory therapy is applied (step 1218). Excitatory therapy may include electrical stimulation having excitatory characteristics (or applied to a pathway that tends to excite the target area) or the release of a therapeutic agent having excitatory effects. If the patient's metabolic rates are abnormally high (step 1220) in comparison to the baseline, inhibitory therapy is applied (step 1222). Inhibitory therapy may include electrical stimulation having inhibitory characteristics (or applied to a pathway that tends to inhibit the target area) or the release of a therapeutic agent having inhibitory effects.

Figure 10:
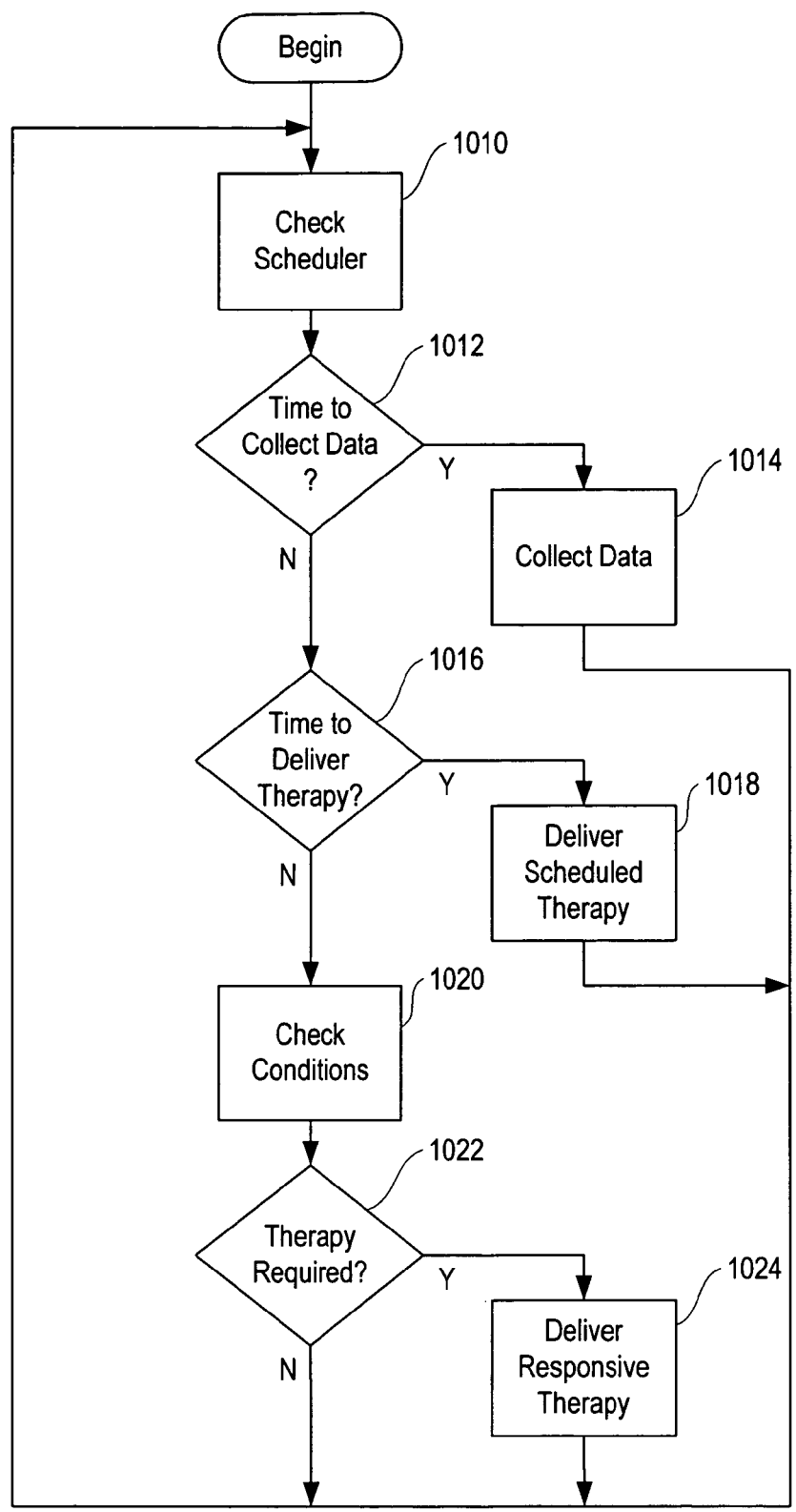
FIG. 10 is a flow chart setting forth an illustrative process performed by hardware functional components of the neurostimulator of FIG. 5 in treating psychiatric disorders according to the invention.

As with depression, the method of treating bipolar disorder preferably includes the ability to correlate observations to information of interest (step 1224), in this case time. As noted, bipolar disorder tends to be cyclic and episodic, and advantages may be obtained by observing patterns in detected symptoms, thereby enabling better scheduled therapy (as illustrated in FIG. 10) or enhanced detection. Later observations of the same or similar data at similar times of day, week, or month would then suggest an episode of depression or mania, even when no patient input is received.

The cingulate cortex is a structure implicated in Obsessive-Compulsive Disorder (OCD) and anxiety disorders. Animal models of anxiety and chronic behavioral stress reveal structural and metabolic changes in the cingulate cortex. Persons with anxiety disorders show abnormally high activation of the cingulate cortex on fMRI during decision making. PET studies in patients with OCD show variable changes in metabolism depending on symptoms. Increased cingulate activation is observed in persons with OCD and significant anxiety while those with compulsive hoarding have decreased cingulate activation. Electroencephalographic abnormalities are also described in persons with OCD. Magnetoencephalography performed in patients with OCD and extreme anxiety revealed paroxysmal rhythmic activity from the cingulate and in other regions of the limbic cortex.

The neurostimulator system described herein promises benefit to persons with OCD and anxiety disorders. Obsessive-compulsive disorder is dynamic in that symptom severity varies over the short-term and long-term. Symptom fluctuations must reflect changes in brain physiology, such as the changes already observed in metabolism and electrical activity. The capacity of the device 110 to record from the cingulate will offer advantages as electroencephalographic markers of disease activity are further defined and if other biological markers are discovered. This provides further capacity to modify therapy in response to dynamic organic processes and to provide responsive stimulation therapy with or without scheduled stimulation.

Figure 13:
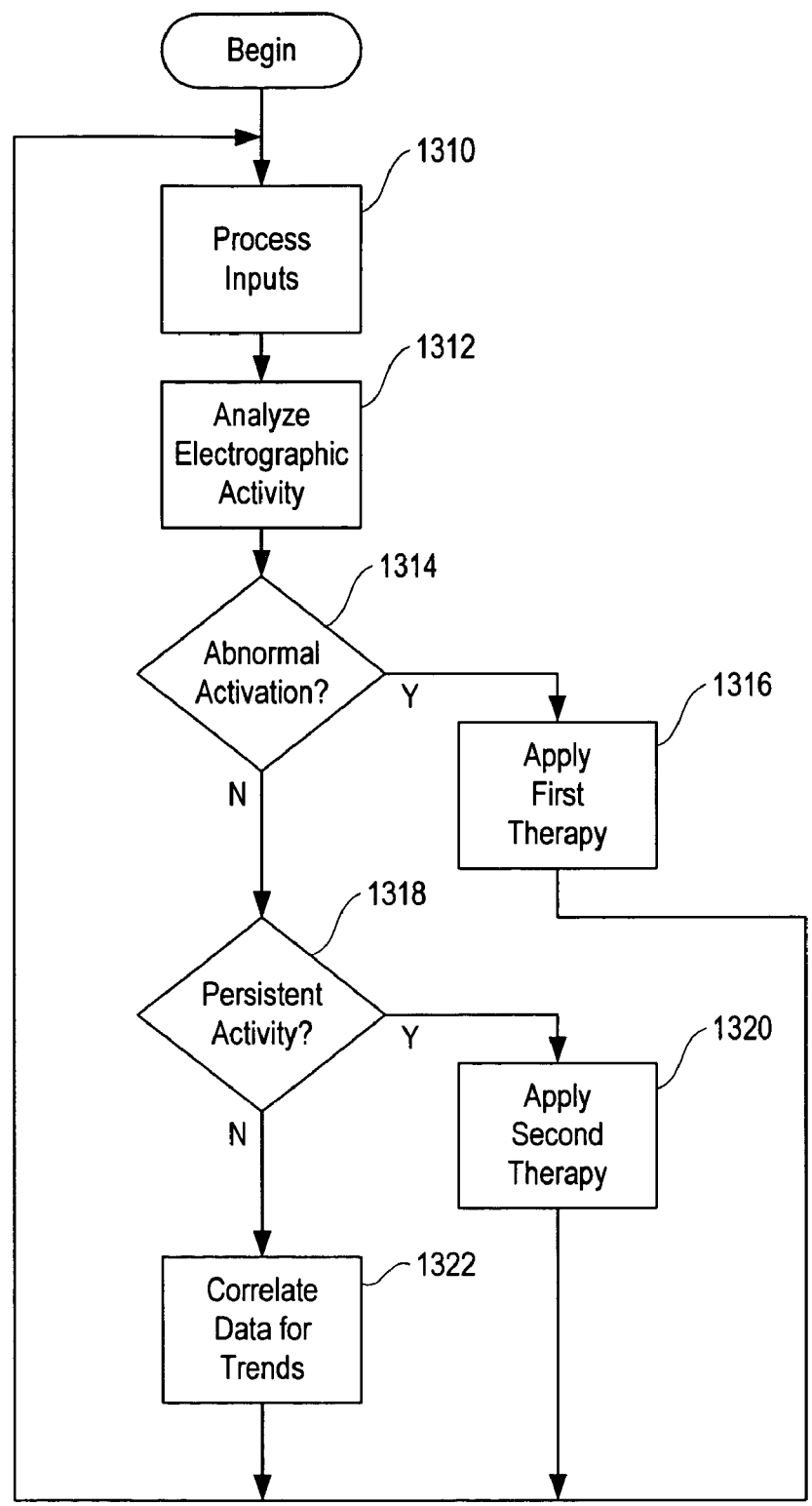
FIG. 13 is a flow chart illustrating a process advantageously used by a system according to the invention to treat anxiety and obsessive-compulsive disorders.

In FIG. 13, a specific method for treating anxiety and obsessive-compulsive disorders begins by receiving inputs (step 1310) and analyzing electrographic activity (step 1312).

If abnormal activation is observed (step 1314), typically by monitoring metabolic rates or electrographic activity in comparison to a baseline level, a first therapy is applied (step 1316). Abnormally high activation would trigger delivery of an inhibitory therapy, while abnormally low activation would trigger excitatory therapy. As above, excitatory therapy may include electrical stimulation having excitatory characteristics (or applied to a pathway that tends to excite the target area) or the release of a therapeutic agent having excitatory effects, while inhibitory therapy may include electrical stimulation having inhibitory characteristics (or applied to a pathway that tends to inhibit the target area) or the release of a therapeutic agent having inhibitory effects.

If persistent abnormal neurologic activity is observed (step 1318), a second therapy is applied (step 1320). The nature of the second therapy may be the same as or different from that of the first therapy, and whether activation or inhibition is desired. The therapy desired in turn may depend on whether the patient tends to exhibit OCD plus anxiety or compulsive hoarding, to name the examples set forth above. Other patient-specific therapies may also be applicable and may depend on clinical observations. When possible, information is collected and correlated with observations to generate trends (step 1322) and improve performance.

Post-Traumatic Stress Disorder (PTSD) is characterized by exaggerated emotional and behavioral responses (hyperarousal) to stimuli associated with a traumatic experience. Many investigators propose that the anterior cingulate—a brain region that appears to be involved in fear-conditioning—is dysfunctional in PTSD. Quantitative MRI reveals a reduction in volume in the cingulate of persons with PTSD. Functional MRI investigations describe significantly less activation of the anterior cingulate gyrus than expected with presentation of stressful stimuli. Observations that chronic behavioral stress induces architectural and neurochemical changes in the cingulate gyrus also suggest that this structure may be an appropriate target for treating PTSD.

Figure 14:
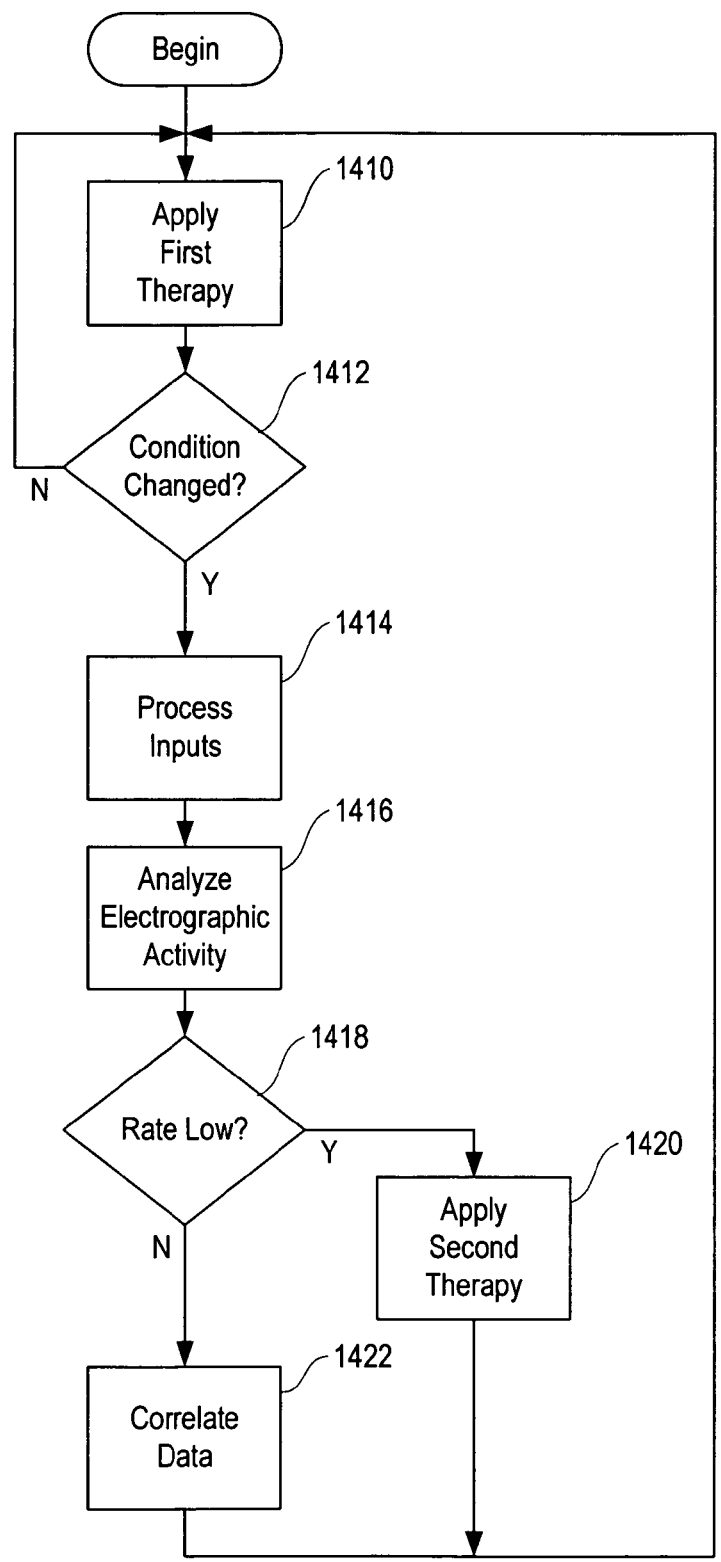
FIG. 14 is a flow chart illustrating a process advantageously used by a system according to the invention to treat post-traumatic stress disorder.

An exemplary specific course of treatment for PTSD using an implantable neurostimulator device 110 is illustrated in FIG. 14. Initially, as PTSD can be characterized by physiological changes, a first course of non-responsive therapy is applied (step 1410). This therapy may include electrical stimulation or any of the other treatment modalities discussed herein. This initial course of therapy is continued until conditions change (step 1412) and improvement is observed.

Following the initial course of therapy and a change in conditions, the neurostimulator device processes inputs (step 1414) and analyzes electrographic or other physiological brain activity (step 1416). If less activation is observed and a low level of electrographic or other brain activity is noted (step 1418), then a second therapy is applied (step 1420), typically excitatory. The nature of the therapy may vary from patient to patient. Finally, where possible, observations of low activation are correlated (step 1422) with stressful stimuli, as indicated by a patient using the initiating device 424 (FIG. 4) or by other means, thereby facilitating analysis of the correlation (either by the device 110 or offline), enhancement of detection parameters, and improved performance in the future.

PET scans in substance addicted individuals display metabolic activation of the cingulate during intoxication, craving and binging. In contrast, there is cingulate hypometabolism during withdrawal. A hypothesis is advanced that changes in dopamine release and in dopamine receptors lead to changes in cingulate metabolic rates during intoxication, withdrawal, and craving. These observations suggest that disease activity can be monitored directly from the cingulate and that modulating cingulate metabolism by providing electrical stimulation therapy may lessen the biologically based withdrawal and craving that leads to relapse.

Figure 15:
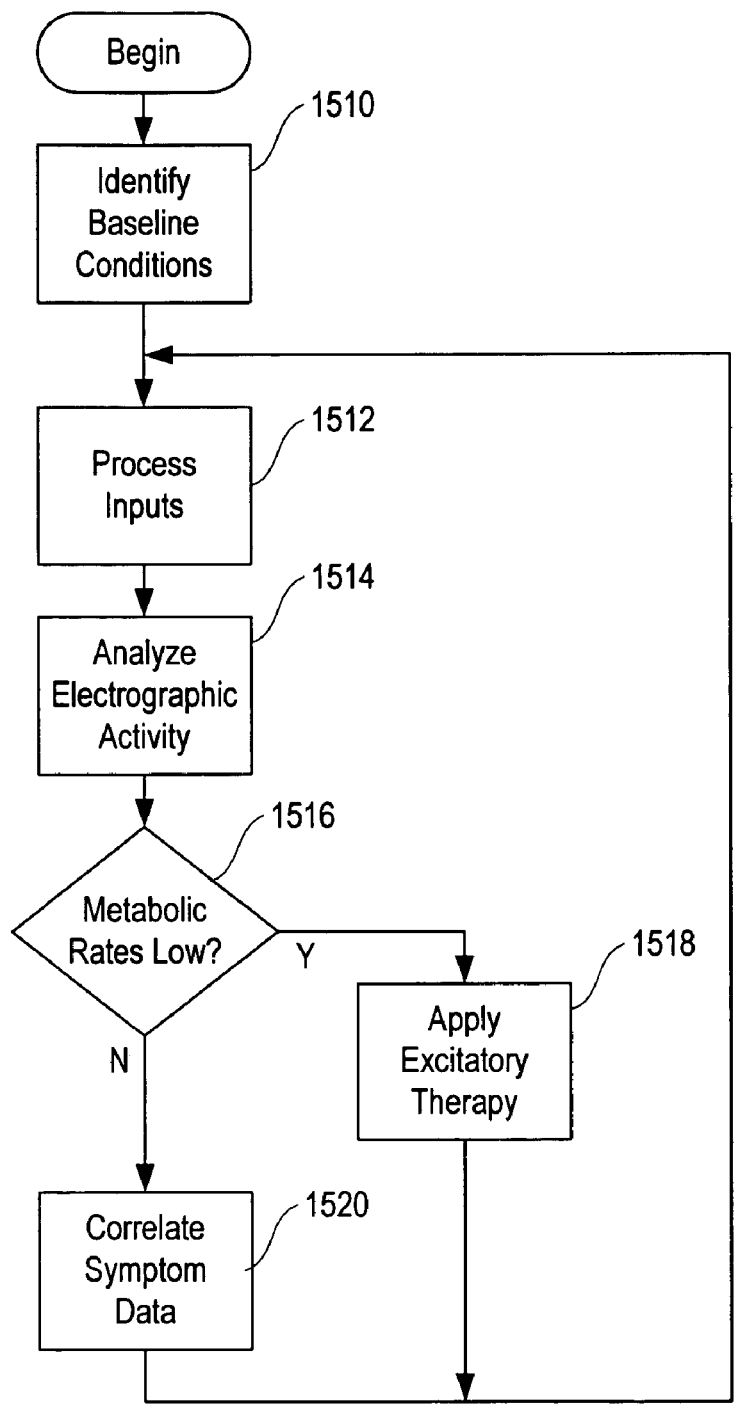
FIG. 15 is a flow chart illustrating a process advantageously used by a system according to the invention to treat addiction.

In a system according to the invention, the hypometabolism observed during withdrawal is sought to be treated as illustrated in FIG. 15. Initially, baseline metabolism conditions are observed (step 1510). Baseline conditions may include typical electrographic activity and other indicia of metabolism as discussed elsewhere in this document. Following that, the neurostimulator device 110 processes inputs (step 1512) and analyzes electrographic activity (step 1514). If the patient's metabolic rates, as determined by observing electrographic activity and other indicia of metabolic rate, are abnormally low (step 1516) in comparison to the baseline, excitatory therapy is applied (step 1518). As stated above, excitatory therapy may include electrical stimulation having excitatory characteristics (or applied to a pathway that tends to excite the target area) or the release of a therapeutic agent having excitatory effects.

Preferably, observations of low metabolic rate are correlated (step 1520) with the patient's symptoms by allowing input via initiating device 424 (FIG. 4). In this manner, the patient can confirm episodes of withdrawal that are observed by the device 110 as periods of low metabolic rate, thereby validating the approach and enabling refinement of detection and therapy according to the invention. Also, the device can enable the patient to self-deliver therapy in response to symptoms of craving or withdrawal, much as patient-delivered devices deliver narcotic medications for pain. The device would be programmed in such a way that the patient would not be able to deliver stimulation or other therapy that could be harmful.

The anterior cingulate cortex (ACC) is a key region within the human prefrontal cortex that has been shown to be dysfunctional in schizophrenic patients. PET scans demonstrate hypometabolism of the cingulate in patients with schizophrenia during cognitive processing tasks as well as in the resting state. Abnormalities in this functional neuroimaging likely reflect underlying disturbances in cingulate anatomy and neurochemistry. Specific reductions in the volume of the cingulate cortex is described by MRI in patients with schizophrenia and is also detected by estimating total cell number in cytoarchitectonically defined areas from the prefrontal cortex. Neurochemical abnormalities described in the cingulate cortex of persons with schizophrenia include a reduction the dopamine D2 receptors and dysfunction of excitatory neurotransmitters such as glutamate.

Persons with schizophrenia have electroencephalographic abnormalities in the cingulate cortex. Electrophysiological recordings from the cingulate cortex in animals and in persons with epilepsy indicate that background activity is similar to that of the hippocampus. However, persons with schizophrenia have poor synchronization of the EEG in the cingulate and abnormalities specifically in frequencies of about 40 Hz. These fast gamma frequencies cannot be detected by scalp EEG but are well represented with intracranial recordings. Persons with schizophrenia also have abnormal electrophysiological activity in the anterior cingulate cortex during various cognitive activation tasks as demonstrated by three-dimensional source location with low-resolution electromagnetic tomography (LORETA), including a significant increase in delta EEG activity.

This critical mass of research supports the premise that therapy targeted to the cingulate cortex will favorably influence schizophrenic symptoms. Anatomical, neurochemical and electrophysiological abnormalities in the resting and activated states will provide biological markers for responsive therapy.

The neurostimulator system provides extensive coverage of the cingulate cortex from it's anterior to posterior extent, which enables anatomically targeted therapy. Continuous recording enables detection of changes in electrographic activity and will provide information critical to refining our understanding of the functional disturbances of the cingulate in this disease state. Accumulating data regarding the electrophysiology of the cingulate in schizophrenia will also be key to optimizing electrical stimulation therapy—both to correct any basal abnormalities as well as to respond to event related electrical disturbances.

Figure 16:
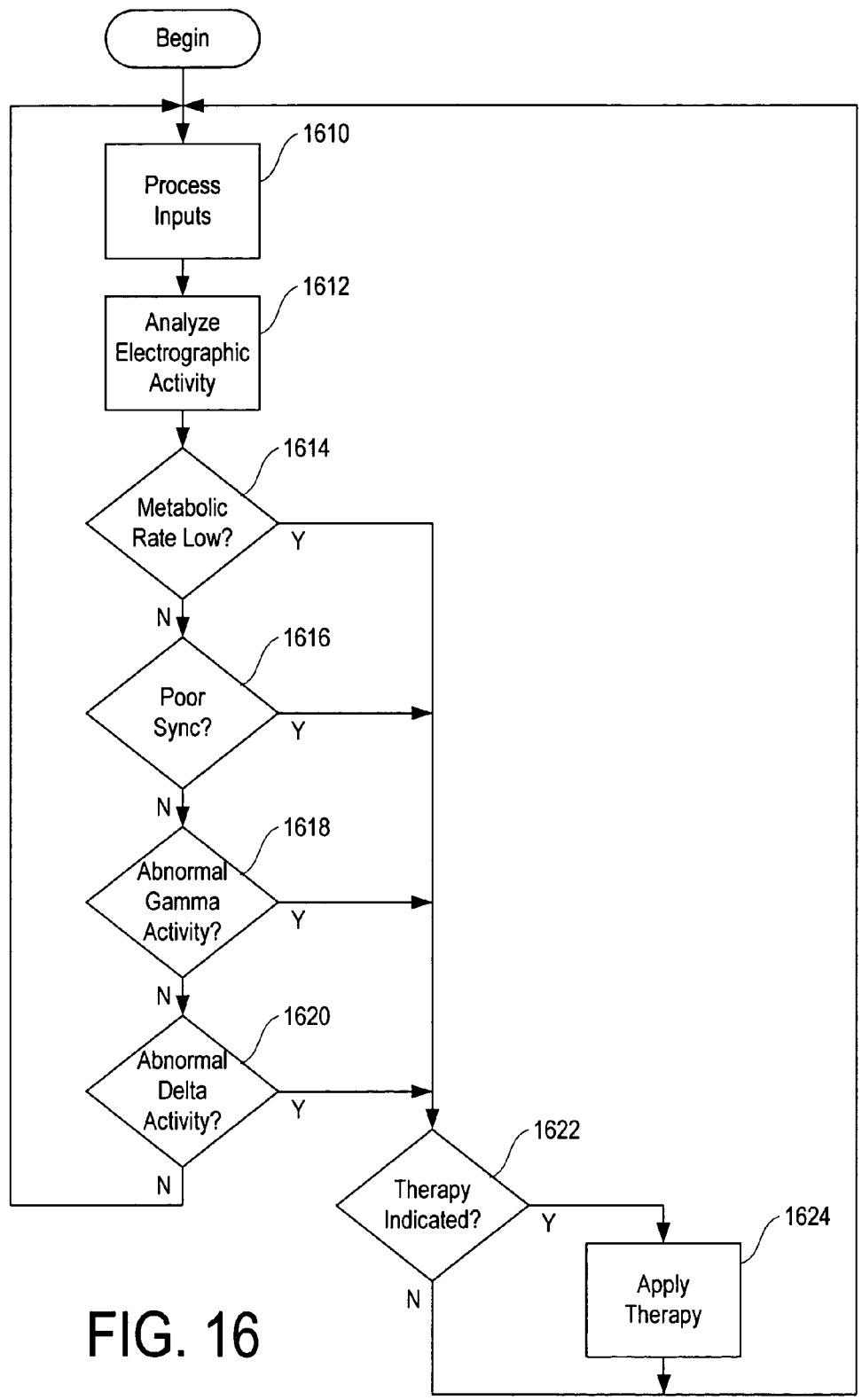
FIG. 16 is a flow chart illustrating a process advantageously used by a system according to the invention to treat schizophrenia.

In FIG. 16, a specific method for treating schizophrenia begins by receiving inputs (step 1610) and analyzing electrographic activity (step 1612). If the patient's metabolic rate is low (step 1614), or poor synchronization is observed (step 1616), or abnormal gamma activity is observed (step 1618), or abnormal delta activity is observed (step 1620), then the totality of circumstances is analyzed to determine whether therapy is indicated (step 1622). If so, then therapy is applied (step 1624), and may be either excitatory or inhibitory, as clinical circumstances dictate.

In a system according to the invention, synchronization (or the lack thereof), and activity in various frequency bands may be determined with an appropriately configured wave morphology analysis unit, such as one that analyzes the duration and amplitude of signal half waves. See e.g., U.S. Pat. No. 6,810,285 to Pless et al. for a detailed description of this process. That application is hereby incorporated by reference as though set forth in full herein. Such a device can respond to the fluctuating symptoms of schizophrenia, such as hallucinations and delusions. This device also provides a distinct advantage to pharmacological therapy. Failure of therapy in persons with schizophrenia is often related to non-compliance. This device removes the need for the patient to remember and be willing to take medications multiple times per day.

Dysfunction of the cingulate cortex is implicated in the social disability associated with autism and pervasive developmental delay. Persons with autism have qualitative impairment in social interaction and communication. The cingulate is believed to be essential for higher cognitive function and in the expression and recognition of affect. Cytoarchitectonic changes are described in the cingulate cortex as well as the hippocampus, subiculum and entorhinal cortex of persons with autism studied post-mortem. Significant reductions in metabolic activity in cingulate gyri are visualized in persons with autism spectrum disorders imaged by PET scans. Stimulation over the cingulate cortex could activate those centers mediating these social behaviors.

There is a high prevalence of epilepsy in persons with autism. Epileptiform discharges are described in medial frontal regions in persons with autism. Similar to frontal lobe epilepsy, these discharges often activate with sleep. Some persons with autism improve cognitively when treated with antiepileptic drugs. A system according to the invention can detect and treat such abnormal electrographic discharges via cortical electrodes placed over the cingulate cortex, as more fully described in U.S. Pat. No. 6,597,954 to Pless et al., issued Jul. 22, 2003 and entitled "SYSTEM AND METHOD FOR CONTROLLING EPILEPTIC SEIZURES WITH SPATIALLY SEPARATED DETECTION AND STIMULATION ELECTRODES", which is hereby incorporated by reference as though set forth in full herein, and others.

Figure 17:
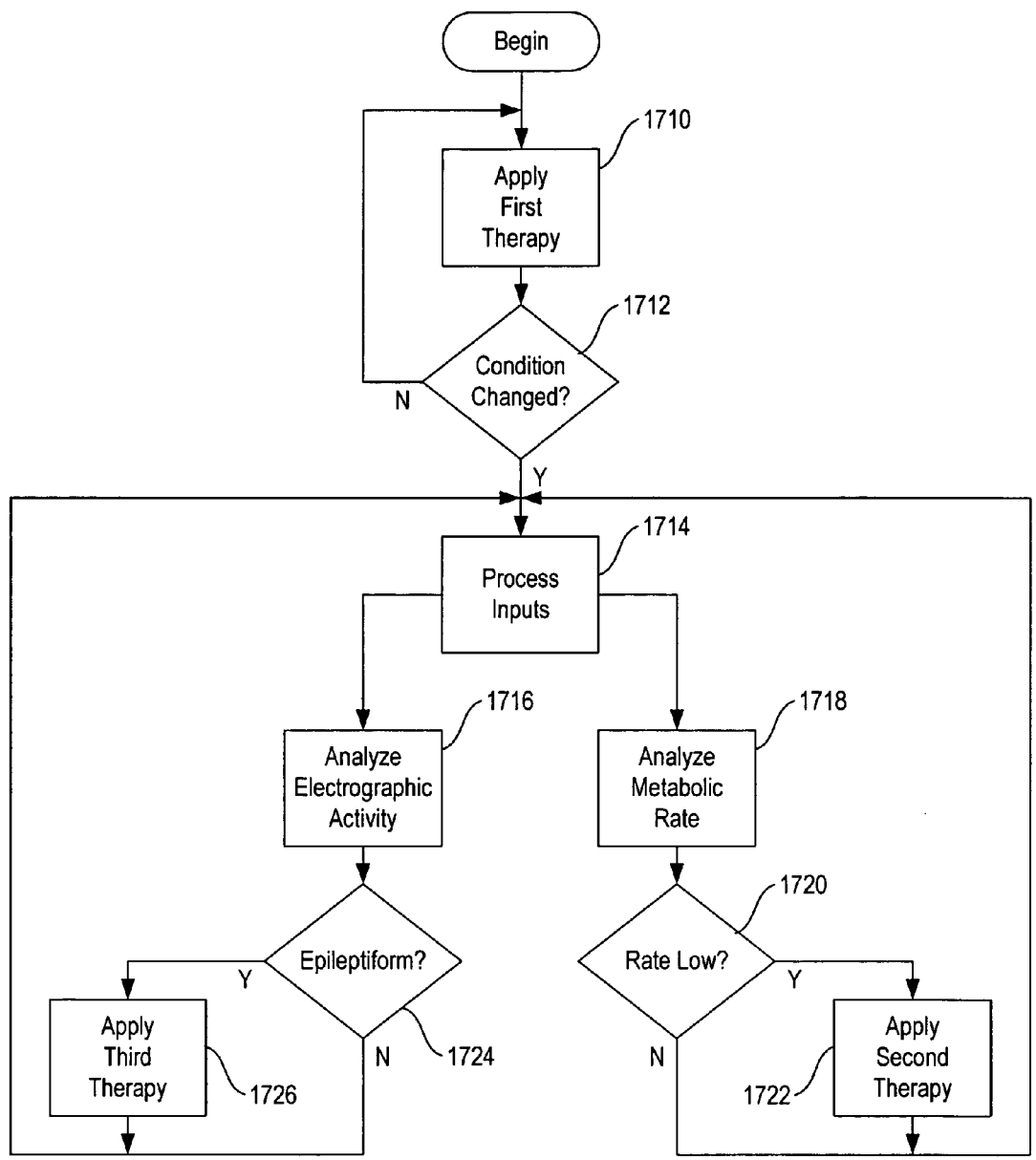
FIG. 17 is a flow chart illustrating a process advantageously used by a system according to the invention to treat autism and other developmental disorders.

An exemplary method according to the invention for treating autism is illustrated in FIG. 17, on the premise that a short-term depression in metabolic rate may be indicative of increased symptoms. Initially, as autism and certain developmental disorders are characterized by physiological changes, a first course of non-responsive therapy is applied (step 1710). This therapy may include electrical stimulation or any of the other treatment modalities discussed herein. This initial course of therapy is continued until conditions change (step 1712) and improvement is observed.

Following the initial course of therapy and a change in conditions, the neurostimulator device processes inputs (step 1714). Then, essentially in parallel, electrographic activity is analyzed (step 1716) and metabolic rate is analyzed (step 1718). If the metabolic rate is abnormally low (step 1720), a second course of therapy, typically excitatory, is provided (step 1722) to correct the level of function. At substantially the same time, if epileptiform electrographic activity is observed (step 1724), then an appropriate third therapy is delivered (step 1726). For details on an exemplary method for detecting and treating undesired epileptiform activity, see U.S. Pat. No. 6,810,285, referenced above.

Figure 18:
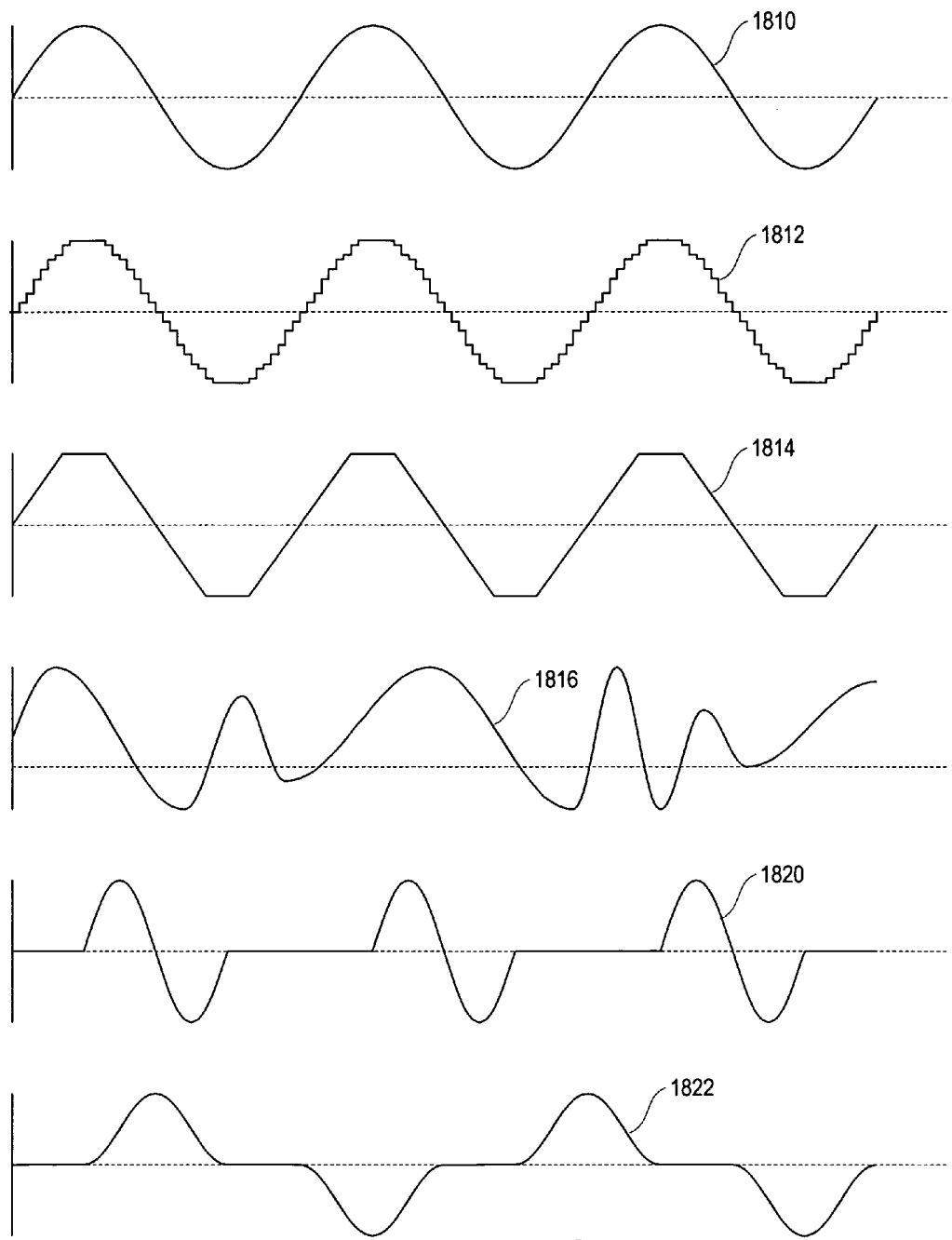
FIG. 18 illustrates a set of therapy waveforms for electrical stimulation that may be used by a neurostimulator according to the invention to treat psychiatric disorders.

Referring now to FIG. 18, in addition to traditional biphasic pulse waveforms used for neurostimulation, other wave morphologies may have advantageous applications herein. A sinusoidal stimulation signal 1810 can be produced and used for non-responsive or responsive brain stimulation according to the invention. In general, sinusoidal and quasi-sinusoidal waveforms may be delivered at low frequencies to have an inhibitory effect, where low frequencies are 0.5 to 10 Hz delivered for 0.05 to 60 minutes at a time. Such waveform may be applied as a result of determining that inhibition is desired on a scheduled basis, or after conditions indicate that responsive stimulation should be applied. Higher frequency sinusoidal or quasi-sinusoidal waveforms may be used for activation. Amplitudes in the range of 0.1 to 10 mA would typically be used, but attention to safe charge densities is important to avoid neural tissue damage (where a conservative limit is 25 $\mu C/cm^2$ per phase). It should be noted that the inhibitory and activating functions of various sinusoidal stimulation parameters may vary when applied to different parts of the brain; the above is merely exemplary.

Sinusoidal and quasi-sinusoidal waveforms presented herein would be constructed digitally by the therapy subsystem 524 (FIG. 5) of the implanatable neurostimulator device 110. As a result, the sinusoid 1810 is really generated as a stepwise approximation, via a series of small steps 1812. The time between steps is dependent upon the details of the waveform being generated, but an interval of 40 microseconds has been found to be a useful value. It is anticipated that the stair step waveform 1812 may be filtered to arrive at a waveform more similar to 1810, which would allow for longer periods of time between steps and larger steps. Likewise, for the waveforms 1816, 1820, and 1822 (described below), it is assumed that they may be created with a series of steps notwithstanding their continuous appearance in the figures.

A truncated ramp waveform 1814 is also possible, where the rate of the ramp, the amplitude reached and the dwell at the extrema are all selectable parameters. The truncated ramp has the advantage of ease of generation while providing the physiological benefits of a sinusoidal or quasi-sinusoidal waveform.

A variable sinusoidal waveform 1816 where the amplitude and frequency are varied while the waveform is applied is also illustrated. The rate and amplitude of the variation may be varied based upon a predefined plan, or may be the result of the implanted neurostimulator sensing signals from the brain during application or between applications of the waveform, and adjusting to achieve a particular change in the sensed signals. The variable waveform 1816 is illustrated herein as having a positive direct current component, but it should be noted that this waveform, as well as any of the others described herein as suitable for use according to the invention, may or may not be provided with a direct current component as clinically desired.

Waveforms 1820 and 1822 depict variations where the stimulating waveform is generated having a largely smooth waveform, but having the additional feature where the interval between waveforms is set by varying a selectable delay, as would be used with the traditional biphasic pulse waveforms described previously. In waveform 1820, the stimulating waveforms are segments of a sine wave separated in time (of course the same technique could be used for the truncated ramp, or other arbitrary morphologies). Waveform 1822 shows a variation where the derivative in time of the waveform approaches zero as the amplitude approaches zero. The particular waveform 1822 is known as a haversine pulse.

Although the term "haversine pulse" is useful to describe the waveform of 1822, it should be noted that all of the waveforms presented in FIG. 18 are considered herein to be generally "non-pulsatile," in contrast with waveforms made up of traditional discontinuous (e.g., square) pulses. As the term is used herein, "non-pulsatile" can also be applied to other continuous, semi-continuous, discontinuous, or stepwise-approximated waveforms that are not exclusively defined by monophasic or biphasic square pulses.

In the disclosed embodiment, the default stimulation behavior provided by a neurostimulator according to the invention is to stimulate with charge-balanced biphasic pulses. This behavior is enforced by stimulation generation hardware that automatically generates a symmetric equal-current and equal-duration but opposite-polarity pulse as part of every stimulation pulse; the precise current control enabled by the present invention makes this approach possible. However, the neurostimulator is preferably programmable to disable the automatic charge balancing pulse, thereby enabling the application of monophasic pulses (of either polarity) and other unbalanced signals.

Alternatively, if desired, charge balancing can be accomplished in software by programming the neurostimulator to specifically generate balancing pulses or signals of opposite phase. Regardless of whether charge balancing is accomplished through hardware or software, it is not necessary for each individual pulse or other waveform component to be counteracted by a signal with identical morphology and opposing polarity; symmetric signals are not always necessary. It is also possible, when charge balancing is desired, to continuously or periodically calculate the accumulated charge in each direction and ensure that the running total is at or near zero over a relatively long term and preferably, that it does not exceed a safety threshold even for a short time.

To minimize the risks associated with waveforms that are either unbalanced or that have a direct current component, it is advantageous to use electrodes having enhanced surface areas. This can be achieved by using a high surface area material like platinum black or titanium nitride as part or all of the electrode. Some experimenters have used iridium oxide advantageously for brain stimulation, and it could also be used here. See Weiland and Anderson, "Chronic Neural Stimulation with Thin-Film, Iridium Oxide Electrodes," *IEEE Transactions on Biomedical Engineering*, 47: 911-918 (2000).

An implantable version of a system according to the invention advantageously has a long-term average current consumption on the order of 10 microamps, allowing the implanted device to operate on power provided by a coin cell or similarly small battery for a period of years without need for replacement. It should be noted, however, that as battery and power supply configurations vary, the long-term average current consumption of a device according to the invention may also vary and still provide satisfactory performance.

It should be observed that while the foregoing detailed description of various embodiments of the present invention is set forth in some detail, the invention is not limited to those details and an implantable neurostimulator or neurological disorder detection device made according to the invention can differ from the disclosed embodiments in numerous ways. In particular, it will be appreciated that embodiments of the present invention may be employed in many different applications to responsively treat psychiatric disorders. It will be appreciated that the functions disclosed herein as being performed by hardware and software, respectively, may be performed differently in an alternative embodiment. It should be further noted that functional distinctions are made above for purposes of explanation and clarity; structural distinctions in a system or method according to the invention may not be drawn along the same boundaries. Hence, the appropriate scope hereof is deemed to be in accordance with the claims as set forth below.

What is claimed is:

1. A method for treating a psychiatric disorder with an implantable apparatus in a human patient, the method comprising:

receiving a detected signal from a sensor, wherein the sensor is configured to sense information from the cingulate cortex of a patient's brain;

identifying a detected event in the detected signal, wherein the detected signal is characteristic of the psychiatric disorder or a symptom of the psychiatric disorder;

positioning an electrode array so that a plurality of electrodes are positioned within or along the cingulate cortex so that the electrodes cover an area that extends over substantially the entire length of the cingulate cortex;

in response to the detected event, causing a therapy subsystem to apply a therapy using at least one of the electrodes in the electrode array; and recording the information sensed from the cingulate cortex of the patient's brain on a scheduled basis.

2. The method of claim 1, wherein the psychiatric disorder is selected from the group consisting of depression, bipolar disorder, anxiety disorder, and obsessive-compulsive disorder.

3. The method of claim 1, wherein the psychiatric disorder is selected from the group consisting of post-traumatic stress disorder, addiction, schizophrenia, autism, and a developmental disorder.

4. The method of claim 1 further comprising modifying the therapy based on the recorded information.

5. The method of claim 1, wherein the therapy is electrical stimulation.

6. The method of claim 1, wherein the sensor is implemented using at least one of the electrodes in the electrode array.

7. The method of claim 1, wherein recording the information sensed from the cingulate cortex of the patient's brain on a scheduled basis includes recording the information sensed from the cingulate cortex of the patient's brain substantially continuously whenever therapy is and is not being applied.

8. The method of claim 1, wherein recording the information sensed from the cingulate cortex of the patient's brain on a scheduled basis includes recording the information sensed from the cingulate cortex of the patient's brain substantially continuously whenever therapy is not being applied.

* * * * *